(12) United States Patent
Hegg

(10) Patent No.: US 11,504,466 B2
(45) Date of Patent: Nov. 22, 2022

(54) MEDICAL GAUZE AND GAS FLOW ASSEMBLY AND METHOD OF APPLYING A MEDICAL GAUZE WITH GAS FLOW ON A WOUND

(71) Applicant: Jeffrey Hegg, Saint Petersburg, FL (US)

(72) Inventor: Jeffrey Hegg, Saint Petersburg, FL (US)

( * ) Notice: Subject to any disclaimer, the term of this patent is extended or adjusted under 35 U.S.C. 154(b) by 141 days.

(21) Appl. No.: 16/843,499

(22) Filed: Apr. 8, 2020

(65) Prior Publication Data

US 2020/0316273 A1   Oct. 8, 2020

Related U.S. Application Data

(60) Provisional application No. 62/830,594, filed on Apr. 8, 2019.

(51) Int. Cl.
*A61M 1/00*  (2006.01)
*A61F 13/00* (2006.01)
(Continued)

(52) U.S. Cl.
CPC ....... *A61M 1/964* (2021.05); *A61F 13/00068* (2013.01); *A61F 13/0246* (2013.01);
(Continued)

(58) Field of Classification Search
CPC . A61M 1/964; A61M 35/30; A61F 13/00068; A61F 13/0246; A61F 13/069; A61F 2013/00157
See application file for complete search history.

(56) References Cited

U.S. PATENT DOCUMENTS 3,881,477 A * 5/1975 Von Otto ............... A61B 90/40
   128/200.24
4,608,041 A * 8/1986 Nielsen ............. A61F 13/00068
   604/289

(Continued)

FOREIGN PATENT DOCUMENTS

WO   WO-0007653 A1 * 2/2000 .......... A61M 1/0025
WO   2019007874 A1    1/2019

*Primary Examiner* — Susan S Su
*Assistant Examiner* — Eric Rassavong
(74) *Attorney, Agent, or Firm* — Mark C. Johnson; Johnson Dalal

(57) ABSTRACT

A medical gauze and gas flow assembly and method of applying a medical gauze with gas flow over a wound, provides a medical dressing cover that couples to a gas flow framing structure. The gas flow framing structure provides a flow of gas over a wound. A medical grade gauze material adheres to the lower surface of the medical dressing cover, so as to create spacing between the medical grade gauze material and the wound treatment area. The gas flow is directed between the medical grade gauze material and the wound treatment area. The gas flow vents to ambient though the gas permeable medical dressing cover. When degraded, the assembly is replaced or only the medical dressing cover and medical grade gauze material is replaced. The synergistic combination of a medical grade gauze material that is a gas permeable, with a gas flow structure that discharges gas over the wound enhances healing the wound.

17 Claims, 18 Drawing Sheets

(51) Int. Cl.
 *A61M 35/00* (2006.01)
 *A61F 13/06* (2006.01)
 *A61F 13/02* (2006.01)

(52) U.S. Cl.
 CPC ........... *A61F 13/069* (2013.01); *A61M 35/30* (2019.05); *A61F 2013/00157* (2013.01)

(56) References Cited

U.S. PATENT DOCUMENTS

| | | |
|---|---|---|
| 5,578,022 A | 11/1996 | Scherson |
| 5,855,570 A | 1/1999 | Scherson |
| 6,000,403 A | 12/1999 | Cantwell |
| 6,465,708 B1 * | 10/2002 | Augustine ............. A61M 35/00 602/41 |
| 6,767,342 B1 * | 7/2004 | Cantwell ........... A61F 13/00068 424/447 |
| 8,287,506 B2 | 10/2012 | Wells et al. |
| 8,439,860 B2 | 5/2013 | Cali |
| 8,758,291 B2 | 6/2014 | Schaefer |
| 8,978,265 B2 * | 3/2015 | Parker ............... A61F 13/00051 604/320 |
| 9,592,160 B2 | 3/2017 | Bacon |
| 10,105,265 B2 | 10/2018 | Niederauer et al. |
| 10,179,196 B2 | 1/2019 | Pratt |
| 2003/0212357 A1 | 11/2003 | Pace |
| 2008/0097282 A1 * | 4/2008 | Hole .................... A61K 9/7007 604/23 |
| 2009/0036873 A1 | 5/2009 | Nielson |
| 2010/0217177 A1 * | 8/2010 | Cali ....................... A61P 17/02 604/23 |
| 2011/0015565 A1 * | 1/2011 | Hursey ................. A61M 35/30 604/24 |
| 2012/0022436 A1 * | 1/2012 | Bradley ................ A61M 35/30 604/23 |
| 2012/0289890 A1 | 11/2012 | Sarangapani |
| 2015/0196694 A1 * | 7/2015 | Eckert .................... A61M 1/85 604/24 |
| 2016/0256638 A1 * | 9/2016 | Sarangapani ..... A61F 13/00063 |
| 2019/0001107 A1 | 1/2019 | Niederauer |
| 2019/0030224 A1 * | 1/2019 | Lin ........................ A61L 15/58 |
| 2019/0125945 A1 | 5/2019 | Long |

* cited by examiner

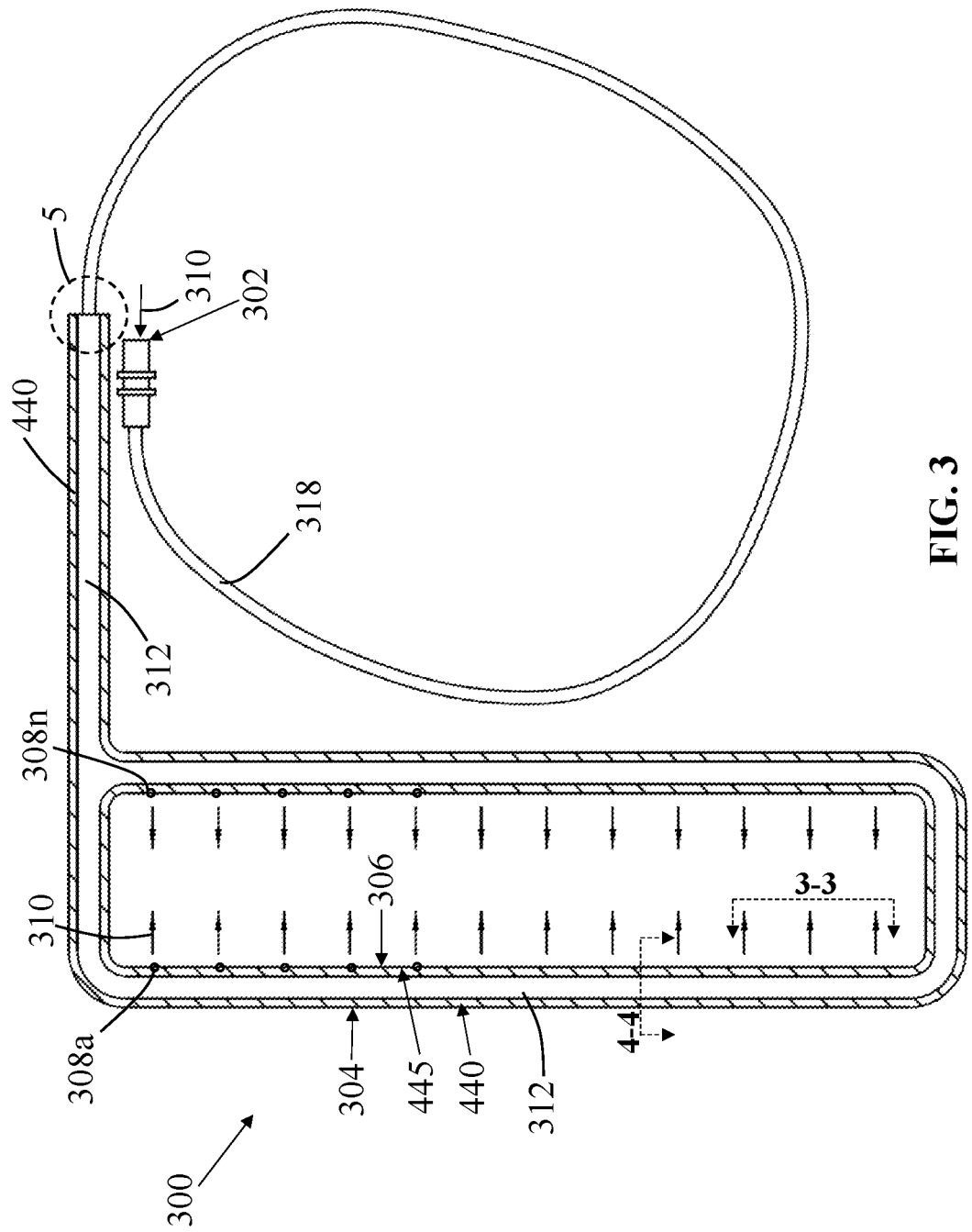

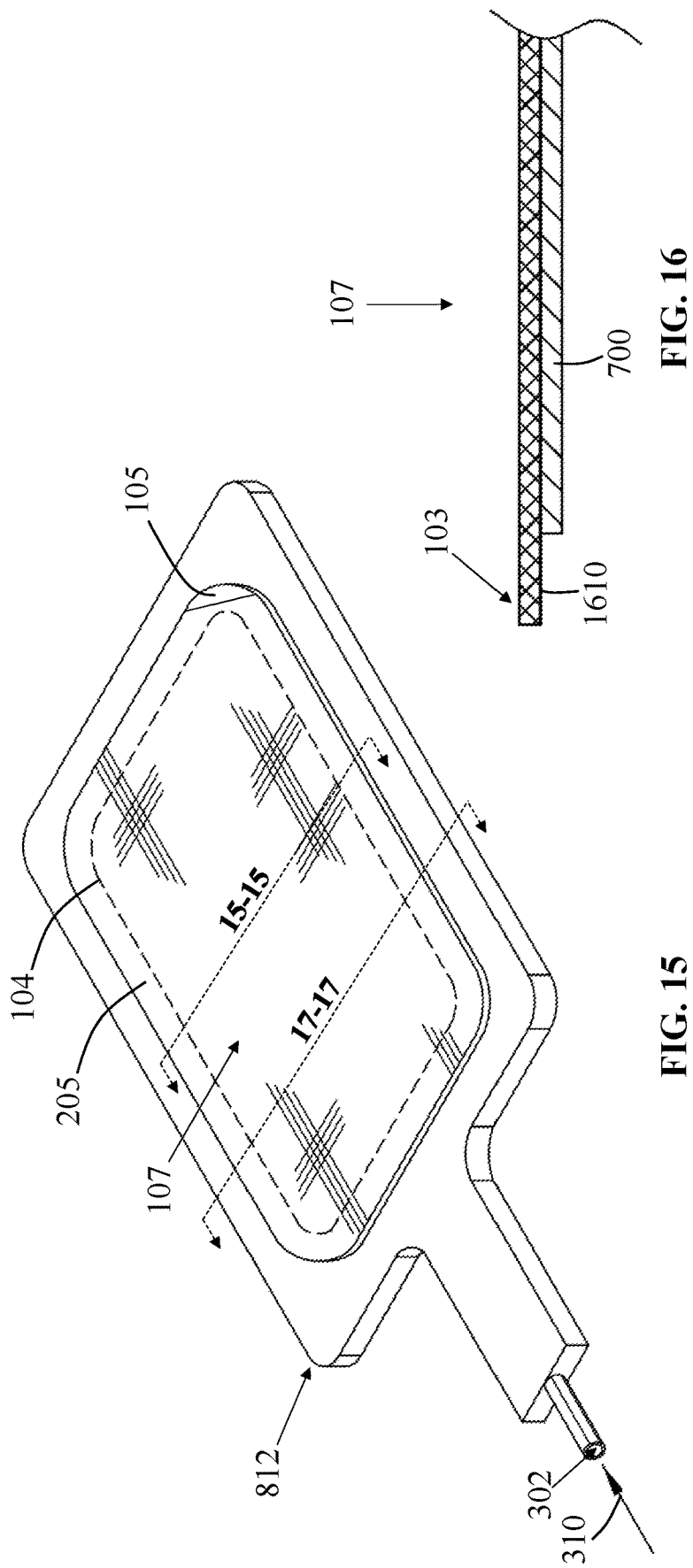

MEDICAL GAUZE AND GAS FLOW ASSEMBLY AND METHOD OF APPLYING A MEDICAL GAUZE WITH GAS FLOW ON A WOUND

CROSS-REFERENCE TO RELATED APPLICATION

This application claims priority to U.S. Provisional Patent Application No. 62/830,594, filed Apr. 8, 2019, the entirety of which is incorporated by reference.

FIELD OF THE INVENTION

The present invention relates generally to wound dressings, and, more particularly, relates to a medical gauze and gas flow assembly and method of applying a medical gauze with gas flow on a wound that is operably configured to absorb wound exudate and flow a gas over a wound treatment area for enhanced healing of the wound using standard respiratory gas sources. The wound may include a laceration, burn, pressure ulcers, bed sores, decubitus ulcers or other superficial wounds known in the medical art.

BACKGROUND OF THE INVENTION

Typically, treating a wound on the skin requires the application of a homogenous wound dressing, often made of woven cotton threads. The wound dressing is laid over the entire wound area to keep the wound clean, and to protect the wound from external contaminants and direct physical trauma. The dressing is also useful for absorbing bodily fluids from the wound, while maintaining a level of ventilation. The wound dressing is held in location with an adhesive attachment to the skin around the perimeter of the wound.

Often, such dressings include a medical grade gauze. The medical grade gauze overlays the wound, providing ventilation, and capacity to absorb bodily fluids, such as wound exudate. The gauze can often be a thin, translucent fabric with a loose open weave. Such a weave structure includes weft yarns that are arranged in pairs and crossed before and after each weft yarn for structural integrity, which is important for stretching across a wound while also retaining air permeability.

Wound treatment also utilizes Topical Oxygen Therapy (TOT) through the application of oxygen gas to the wound surface. The distribution of gas over a wound at high flow rates (greater than 1 litter/min) is enabled by "Bandage/Diaper Aeration Device" as described in U.S. Pat. No. 8,978,265. As described, this bandage/diaper drying system achieves gas flow over the wound and is attached to a secondary device such as a bandage wrap or a diaper. The functions of absorbing wound exudate, holding the device in location over the wound and directing the gas flow is controlled by these secondary devices.

Utilization of multiple devices for wound care increases complexity and cost for treatment. Combining a medical grade gauze with gas flow over the wound provides improved wound care efficacy. As such, a medical gauze and gas flow assembly wound care product that combines multiple devices also results in reduced complexity and cost for wound treatment.

Therefore, a need exists to overcome the problems with the prior art as discussed above.

SUMMARY OF THE INVENTION

The invention provides a medical gauze and gas flow assembly and method of applying a medical gauze with gas flow over a wound that overcomes the hereinafore-mentioned disadvantages of the heretofore-known devices and methods of this general type with a medical dressing cover that couples to a gas flow framing structure directly coupling the gas flow framing structure to a medical dressing cover lower surface. The gas flow framing structure generates a flow of a gas over a wound treatment area. The gas flow is directed over the wound and through the medical dressing cover to the ambient environment. The medical dressing cover includes the medical grade gauze material that is located on the lower surface of the upper layer of the medical dressing cover and is covering the wound. The synergistic combination of a medical grade gauze material that is gas permeable and does not stick to wounds, with a gas flow framing structure that discharges provided gas over the wound treatment area enhances the efficacy for healing a wound. When degraded, the complete medical gauze and gas flow assembly attached to the skin is removed and replaced or the medical dressing cover can be removed and replaced by detaching a replaceable medical dressing cover, and applying a fresh medical grade gauze material reusing the gas flow framing structure attached to the skin and maintaining the connections between the gas inlet and the gas source during the wound treatment.

With the foregoing and other objects in view, there is provided, in accordance with the invention, a medical gauze and gas flow assembly that includes a medical dressing cover. The medical dressing cover is defined by a gas-permeable and flexible upper layer with an upper surface, and a flexible lower layer with an upper surface directly coupled to the lower surface of the upper layer. The medical dressing cover also has a removable flexible polymeric release liner on the medical dressing cover lower surface attached to adhesive located on the perimeter of the lower surface of the upper layer. The release liner is removed prior to usage exposing the adhesive that provides attachment to the skin around the wound. The adhesive has properties common to existing wound care products that enables easy-on, easy-off skin interface (such as silicone-based adhesives).

The medical gauze and gas flow assembly also provides a medical grade gauze material that forms a portion of the lower surface of the medical dressing cover. From this orientation, the medical grade gauze material adheres to the lower surface of the medical dressing cover upper layer, is located over the wound inside the perimeter of the gas flow framing structure and inside the attachment to the skin.

The medical gauze and gas flow assembly also provides a gas flow framing structure, utilized to discharge a provided gas over the wound treatment area. The gas flow framing structure is configured to couple to the medical dressing cover. In one non-limiting embodiment, the gas flow framing structure is directly coupled to the lower surface of the medical dressing cover. The gas flow framing structure comprises an upper surface, a lower surface opposing the upper surface with the upper surface directly coupled to the lower surface of the upper layer of the medical dressing cover.

The gas flow framing structure may include and define a gas inlet for introducing gas into a gas flow channel within the gas flow framing structure formed between the upper and lower layers of the gas flow framing structure. The inner surface is defined by a plurality of enclosed gas outlets, downstream of the gas inlet. The enclosed gas outlets are configured to orient the provided gas flow over a wound treatment area disposed directly above the wound. The gas discharges from the plurality of gas outlets and flows through the medical dressing cover to ambient, described above.

In accordance with a further feature of the present invention, the assembly further comprises a plurality of elastic valves defining the plurality of enclosed gas outlets disposed on the inner surface of the gas flow framing structure.

In accordance with a further feature of the present invention, the plurality of elastic valves comprising slots between the upper and lower layers on the inner perimeter area of the gas flow framing structure operable to allow passage of the provided gas when a predetermined amount of gas pressure is applied to the gas inlet. The plurality of elastic valves comprises a slot operable to allow passage of the provided gas when a predetermined amount of gas pressure is applied to the gas inlet.

In accordance with a further feature of the present invention, the medical dressing cover further comprises a lower surface perimeter with the adhesive disposed thereon.

In accordance with a further feature of the present invention, the lower surface perimeter of the medical dressing cover surrounds the medical grade gauze material.

In accordance with a further feature of the present invention, the gas flow channel within the gas flow framing structure substantially surrounds the medical grade gauze material.

In accordance with a further feature of the present invention, the medical dressing cover has a lower surface perimeter with the adhesive disposed thereon for attachment to the skin. The lower surface around the perimeter contains a detachment tab corner area or protrusion that does not have adhesive.

In accordance with a further feature of the present invention, the medical dressing cover further comprises an upper layer of a gas-permeable material and with a lower surface directly coupled to the medical grade gauze material, the lower surface of the upper layer opposing the upper surface of the medical grade gauze material layer. The lower surface of the medical grade gauze material is located directly over the wound.

In accordance with a further feature of the present invention, the plurality of enclosed gas outlets are disposed on the inner surface of the gas flow framing structure in a parallel, spaced-apart relationship. The plurality of enclosed gas outlets are operably configured to orient the provided gas flow between to the medical grade gauze material forming the lower surface of the medical dressing cover and the wound treatment area, and the gas flows through the gas-permeable and flexible upper and lower layers of the medical dressing cover.

In accordance with a further feature of the present invention, the upper layer of the medical dressing cover is gas-permeable or liquid-permeable.

In accordance with a further feature of the present invention, the plurality of enclosed gas outlets are operably configured to orient the provided gas therethrough and to a wound treatment area disposed below the medical grade gauze material attached to the lower surface of the medical dressing cover upper layer, and then flows through the medical grade gauze material and through the gas-permeable and flexible upper layer of the medical dressing cover to ambient.

In accordance with a further feature of the present invention, the gas flow framing structure is directly coupled to the lower surface of the medical dressing cover.

In accordance with a further feature of the present invention, the medical grade gauze material is disposed directly above the wound treatment area.

In accordance with a further feature of the present invention, the medical grade gauze material absorbs fluids from the wound treatment area.

In accordance with a further feature of the present invention, the gas flow channel within the gas flow framing structure contains a hard-plastic spiral tubing that transverses the length of the gas flow channel.

In accordance with a further feature of the present invention, the gas flow framing structure lower surface is directly coupled to a comfort layer around the perimeter of the wound treatment area made of soft cotton or equivalent.

In accordance with a further feature of the present invention, the plurality of layers are coupled together such that the upper layer is the medical dressing cover, the middle layer is the medical dressing gauze material and the lower layer is the gas flow framing structure, the lower layer of the gas flow framing structure has adhesive disposed upon for attachment to the skin, and a detachment tab corner area or protrusion without adhesive.

In accordance with a further feature of the present invention, the gas flow framing structure couples to a upper foam stand-off layer located between the medical dressing cover and the gas flow framing structure upper surface and to a lower foam stand-off layer located between the lower surface of the gas flow framing structure and the skin, around the perimeter of the wound treatment area.

In accordance with a further feature of the present invention, a gas flow support frame is coupled to the gas flow framing structure, with an upper surface and an lower surface opposing the upper surface of the gas flow support frame, coupling to the inner perimeter of the lower surface of the gas flow support frame to the upper surface of the gas flow framing structure, an adhesive disposed around the outer perimeter of lower surface of the gas flow support frame, a flexible polymeric release liner selectively removably coupled to the lower surface of the gas flow support frame; a lower surface perimeter with the adhesive disposed thereon for attachment to the skin. The lower surface around the perimeter contains a detachment tab on a corner area or protrusion that does not have adhesive.

In accordance with a further feature of the present invention, a replaceable medical dressing cover has a lower surface perimeter with the adhesive disposed thereon for a removable attachment to the gas flow support structure. The lower surface around the perimeter contains a detachment tab on a corner area or protrusion that does not have adhesive. The adhesive material coupling the lower surface of the outer layer of the replaceable medical dressing cover to the upper surface of the gas flow support frame is of a bonding strength property equal to or less than a bonding strength of the adhesive disposed on the lower surface of the gas flow support frame attached to the skin.

In accordance with the present invention, a method of applying a medical gauze with gas flow assembly on a wound provides an efficacious means for healing a wound with a medical gauze and a gas flow framing structure. The method may include an initial Step of identifying a wound treatment area on the skin. The method may further comprise a Step of providing a medical dressing cover having a gas-permeable upper and lower layer, an adhesive on the perimeter of the lower surface on lower layer of the upper layer of the medical dressing cover, and a polymeric release liner selectively removably coupled to lower surface of the upper layer. A Step adhering a medical grade gauze material upper surface to the lower surface of the upper layer of the medical dressing cover, the medical grade gauze material being disposed directly above the wound treatment area.

In some embodiments, a Step comprises coupling a gas flow framing structure to the medical dressing cover, the gas flow framing structure defining a gas inlet, a gas flow channel within the upper and lower layers of the gas flow framing structure, and a plurality of enclosed gas outlets operably configured to orient the provided gas flow therethrough. Use spiral tubing in the gas flow channel wound dressing with bodily compression of the wound dressing. A Step orienting the lower surface of the medical dressing cover towards the wound treatment area.

In some embodiments, a Step may include introducing the provided gas flow into the gas inlet of the gas flow framing structure, the provided gas pressure inflates the gas flow channel. A Step comprises directing the provided gas flow through the enclosed gas outlets between the medical grade gauze material forming the lower surface of the medical dressing cover and the wound treatment area, and the gas flows through the gas-permeable and flexible upper and lower layers of the medical dressing cover. The method may further comprise a Step of removing the complete medical gauze and gas flow assembly from the skin or detaching the replaceable medical dressing cover from the gas flow support frame. A final Step includes replacing the complete medical gauze and gas flow assembly or the replaceable medical dressing cover for a fresh medical grade gauze material.

Although the invention is illustrated and described herein as embodied in a medical gauze and gas flow assembly and method of applying a medical gauze with directed gas flow on a wound, it is, nevertheless, not intended to be limited to the details shown because various modifications and structural changes may be made therein without departing from the spirit of the invention and within the scope and range of equivalents of the claims. Additionally, well-known elements of exemplary embodiments of the invention will not be described in detail or will be omitted so as not to obscure the relevant details of the invention.

Other features that are considered as characteristic for the invention are set forth in the appended claims. As required, detailed embodiments of the present invention are disclosed herein; however, it is to be understood that the disclosed embodiments are merely exemplary of the invention, which can be embodied in various forms. Therefore, specific structural and functional details disclosed herein are not to be interpreted as limiting, but merely as a basis for the claims and as a representative basis for teaching one of ordinary skill in the art to variously employ the present invention in virtually any appropriately detailed structure. Further, the terms and phrases used herein are not intended to be limiting; but rather, to provide an understandable description of the invention. While the specification concludes with claims defining the features of the invention that are regarded as novel, it is believed that the invention will be better understood from a consideration of the following description in conjunction with the drawing figures, in which like reference numerals are carried forward. The figures of the drawings are not drawn to scale.

Before the present invention is disclosed and described, it is to be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Also, for purposes of description herein, the terms "upper", "lower", "left," "rear," "right," "front," "vertical," "horizontal," and derivatives thereof relate to the invention as oriented in the figures and is not to be construed as limiting any feature to be a particular orientation, as said orientation may be changed based on the user's perspective of the device. Furthermore, there is no intention to be bound by any expressed or implied theory presented in the preceding technical field, background, brief summary or the following detailed description.

As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. In this document, the term "longitudinal" should be understood to mean in a direction corresponding to an elongated direction of the gas flow framing structure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system.

BRIEF DESCRIPTION OF THE DRAWINGS

The accompanying figures, where like reference numerals refer to identical or functionally similar elements throughout the separate views and which together with the detailed description below are incorporated in and form part of the specification, serve to further illustrate various embodiments and explain various principles and advantages all in accordance with the present invention.

FIG. 3 is a top view of an exemplary prior art gas flow framing structure, in accordance with the present invention;

FIG. 15 is an upper perspective view of the gas flow framing structure coupled to the replaceable medical dressing cover, in accordance with the present invention;

FIG. 16 is an sectioned side view of the replaceable medical dressing cover, showing the upper layer and the lower surface of the upper layer adhered to the medical dressing gauze assembly, the section taken along 15-15 in FIG. 15, in accordance with the present invention;

DETAILED DESCRIPTION

Figure 2:
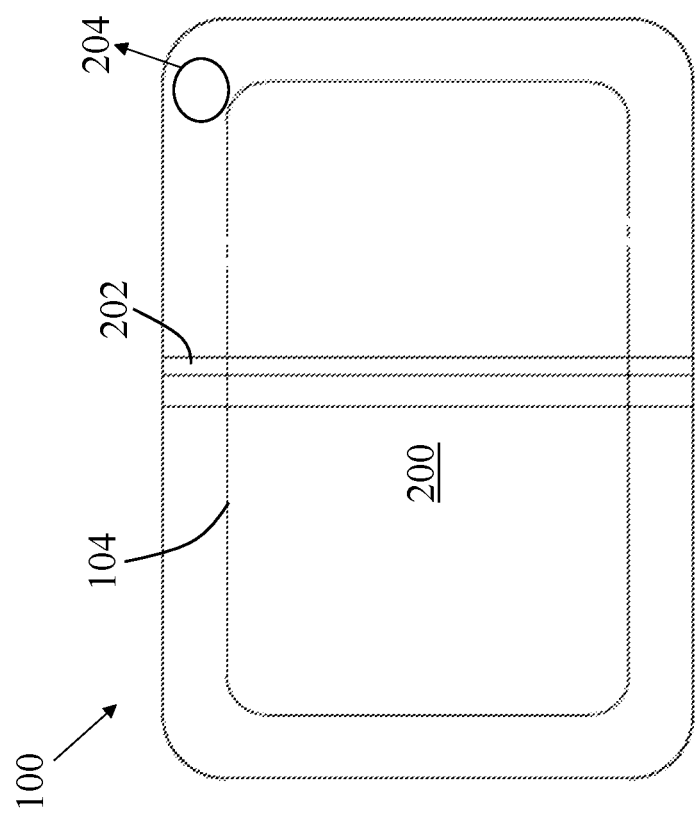
FIG. 2 is a bottom view of the prior art medical dressing cover shown in FIG. 1, in accordance with the present invention.

While the specification concludes with claims defining the features of the invention that are regarded as novel, it is believed that the invention will be better understood from a consideration of the following description in conjunction with the drawing figures, in which like reference numerals are carried forward. It is to be understood that the disclosed embodiments are merely exemplary of the invention, which can be embodied in various forms.

The present invention provides a novel and efficient medical gauze and gas flow assembly 500 and method 2100 of applying a medical gauze with gas flow on a wound. The medical gauze and gas flow assembly 500, hereafter "assembly 500" is configured to flow a gas 310 over a wound treatment area 800 for enhanced healing of the wound, while simultaneously applying a gas-permeable medical grade gauze material 700 to the wound for absorbing fluids and protecting against infections. Embodiments of the invention provide a medical dressing cover 100 that directly couples to a gas flow framing structure 300. The gas flow framing structure 300 provides a flow of gas over the wound treatment area 800.

In addition, embodiments of the invention provide a medical grade gauze material 700 that adheres to the lower surface 804 of the medical dressing cover 100 upper layer 102, so as to create spacing between the medical grade gauze material 700 and the wound treatment area 800. When degraded the complete assembly 500 is removed and replaced by detaching the adhesive between the medical dressing cover lower surface 204 from the skin with a detachment tab 510. In another embodiment, a removable medical dressing cover 103 is removed and replaced by detaching the lower surface 205 of the removable medical dressing cover 103 with a detachment tab 105 and applying a fresh replaceable medical dressing cover 103 thereto. In this embodiment the gas flow assembly 300 attached to the gas flow support frame 812 is reused while remaining fixed to the skin with the connections between the gas inlet 302 and the gas source maintained during replacement of the gauze. The gas flows into the spacing between the medical grade gauze material 700 and the wound treatment area 800 which then flows through the medical grade gauze material 700 and the medical dressing cover upper layer 102,103 to ambient. The medical grade gauze material 700 absorption of exudate in conjunction with the gas flow over the wound treatment area 800 enhances healing.

Figure 1:
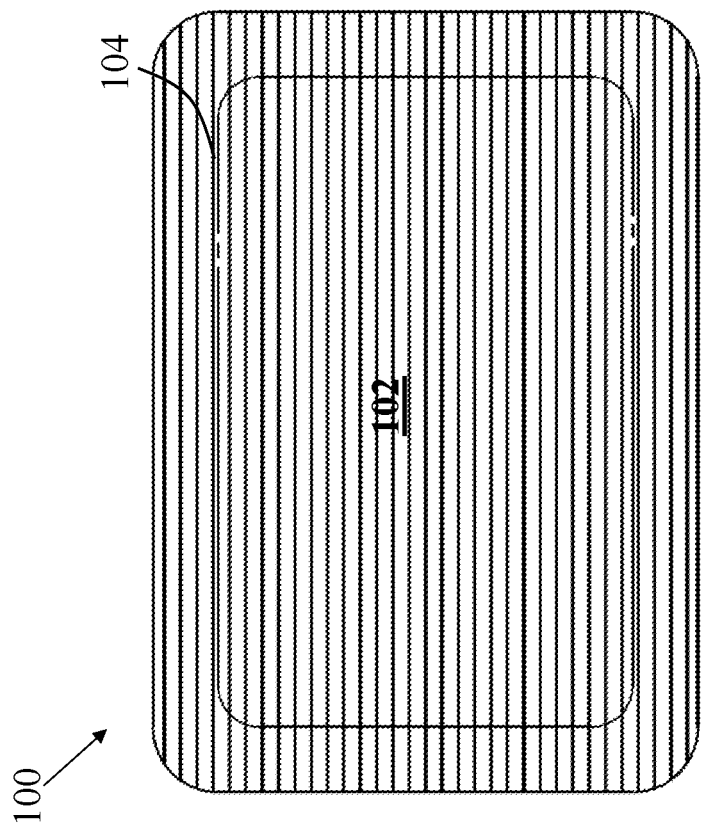
FIG. 1 is a top view of a prior art medical dressing cover, in accordance with the present invention.

FIG. 1 shows several advantageous features of the present invention, but, as will be described below, the invention can be provided in several shapes, sizes, combinations of features and components, and varying numbers and functions of the components. The first example of a prior art, the medical dressing cover 100 is attached to the skin, sized and dimensioned to cover a wound, creates ventilation, and absorbs exudate therefrom. Opposing surfaces of a standard medical dressing cover 100 are illustrated in FIGS. 1-2. The medical dressing cover 100 has a square or rectangular shape with a lower surface 200 that faces the wound and an upper layer 102.

As taught in the present invention, the assembly 500 includes a medical dressing cover 100 that is configured to treat the wound in a wound treatment area 800. The medical dressing cover 100 is defined by a flexible upper layer 102, and a flexible lower layer 200 opposing the upper layer 102. As FIG. 1 shows, the upper surface of the upper layer 102 orients outwardly, being visible and accessible for manipulation and inspection of the medical dressing cover 100. In some embodiments, the upper layer 102 is defined by a woven gas-permeable material or a polymeric or other material that is not gas-permeable configured with an array or distribution of vent holes to achieve gas-permeability. However, the upper layer 102 may also be liquid permeable.

Looking at FIG. 2, an adhesive is disposed on the lower surface 204 of the upper layer 102 medical dressing cover 100 outside the perimeter boundary 104 of the lower layer 200. The adhesive is configured to enable easy-on, easy-off adherence between the medical dressing cover 100 and the skin around the perimeter of the wound treatment area 800. Furthermore, a flexible polymeric release liner 202 is selectively removably coupled to the lower surface 204 and covering the inner surface of the lower layer 200. The release liner 202 overlays the adhesive, such that removing the release liner 202 provides access to the adhesive for attachment to the skin. The lower surface of the lower layer 200 perimeter boundary 104 surrounds an attached medical grade gauze material 700, forming a retention for exudate from the wound treatment area 800. As such, the adhesive is not required to be disposed at the outside perimeter of the lower surface 204, but may be disposed within the outside perimeter of the lower surface 204.

Looking at FIG. 3 another example of prior art, shows several advantageous features of the present invention, but, as will be described below, the invention can be provided in several shapes, sizes, combinations of features and components, and varying numbers and functions of the components. The second example of prior art, the gas flow framing structure 300 is configured to attach to a secondary device such as a bandage wrap or a diaper. For the novel and efficient embodiment herein, the gas flow framing structure 300 top view illustration in FIG. 3 has the following relevant features. The gas flow framing structure 300 is sized and dimensioned to be directly coupled to the medical dressing cover 100 outside the perimeter boundary 104 of lower layer 200. In one embodiment, the gas flow framing structure 300 defines a gas inlet 302 through which a provided gas is introduced. The gas inlet 302 may include a nozzle or tubing through which gas from an external source is introduced. The nozzle or tubing connection, detail 5 from FIG. 3, is sectioned and expanded in FIG. 4d. The gas inlet 302 nozzle or tubing is sandwiched between the upper 410 and lower 420 layers of the gas flow framing structure forming a seal 450 around the nozzle or tubing that allows the input gas 310 to pressurize the gas flow channel 312. The gas inlet 302 nozzle or tubing terminates internal to the gas flow framing structure after the seal.

Figure 4B:
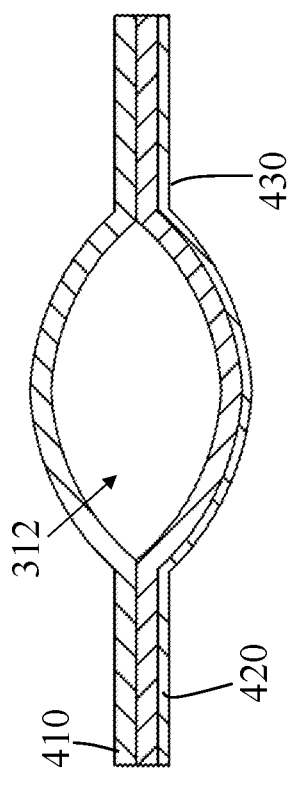
FIGS. 4a-4d are multiple cross-sectional views of the exemplary prior art gas flow framing structure with the present invention (note that the materials are made of very thin layers that are illustrated thicker for clarity).
Figure 4D:
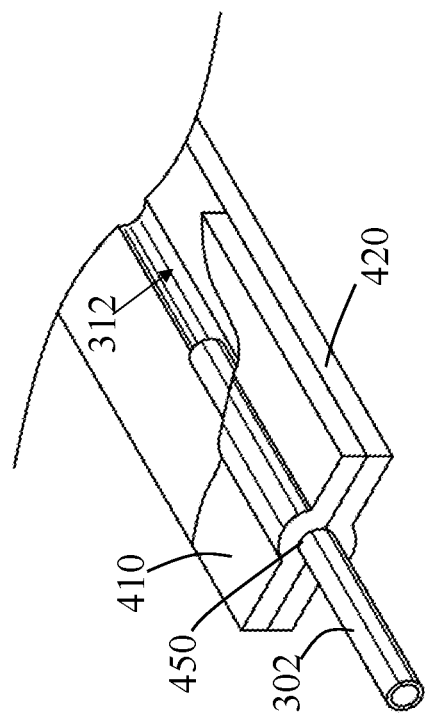
Figure 4A:
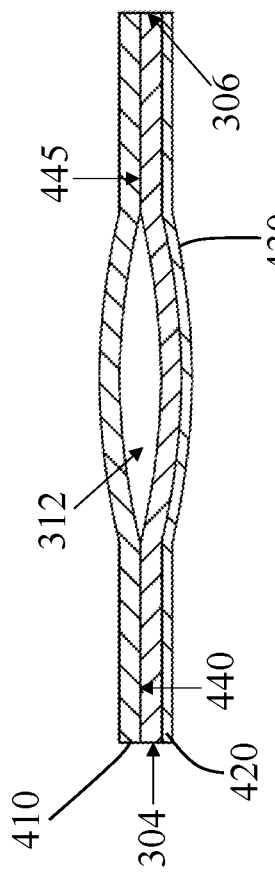
Figure 4C:
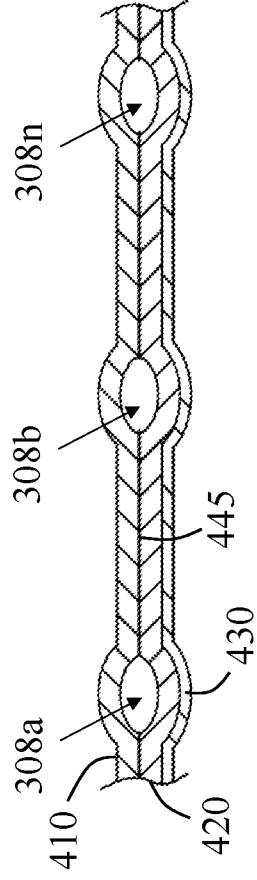

The cross section 4-4 of the gas flow framing structure 300 shown in FIG. 4a consists of three layers of material comprising the prior art for the gas flow framing structure. Upper layer 410 and lower layer 420 are made of very thin sheets of a flexible non-porous material such as plastic. The gas flow channel 312 is formed by directly coupling the upper layer 410 to the lower layer 420 around the external perimeter 304 and the internal perimeter 306. The external perimeter attachment area 440 and the internal perimeter attachment area 445 form the gas flow channel 312. The perimeter attachment areas 440 and 445 are achieved with RF welding of the two materials. The gas distribution channel 312 defined by the enclosed area between external perimeter attachment area 440 and the internal perimeter attachment area 445 and non-permeable materials of the upper 410 and lower 420 layers is very small prior to application of gas pressure to the gas inlet port 302 (as best shown in FIG. 4a). When gas pressure is applied to the gas inlet 302, FIG. 4b illustrates that the gas distribution channel 312 expands due to the stresses created in the thin materials of the upper 410 and lower 420 layers. There are discrete slots within the internal perimeter attachment area 445 where the upper 410 and lower 420 layers are not coupled. FIG. 3 has an end view 3-3 of the inner perimeter 306 that is detailed in FIG. 4c for three adjacent slots. The discrete slots form passages for the gas to flow from the gas flow channel 312 to the gas outlet openings 308a-n illustrated as in FIG. 3 as small circles. When the gas flow channel 312 is pressurized, the stresses in the upper 410 and lower 420 layer materials around the discrete slots open as shown in FIG. 4c allowing the gas to flow into the wound treatment area 800. When gas pressure is removed, the elimination of the stresses causes the slots to close preventing backflow of exudate into the gas flow channel 312. These discrete slots act as elastic valves, opening when pressure is applied and closing when pressure is removed. In the prior art, the inner layer 430 of the gas flow framing structure 300 is a comfort material such as soft cotton to provide an interface to the skin.

Figure 5:
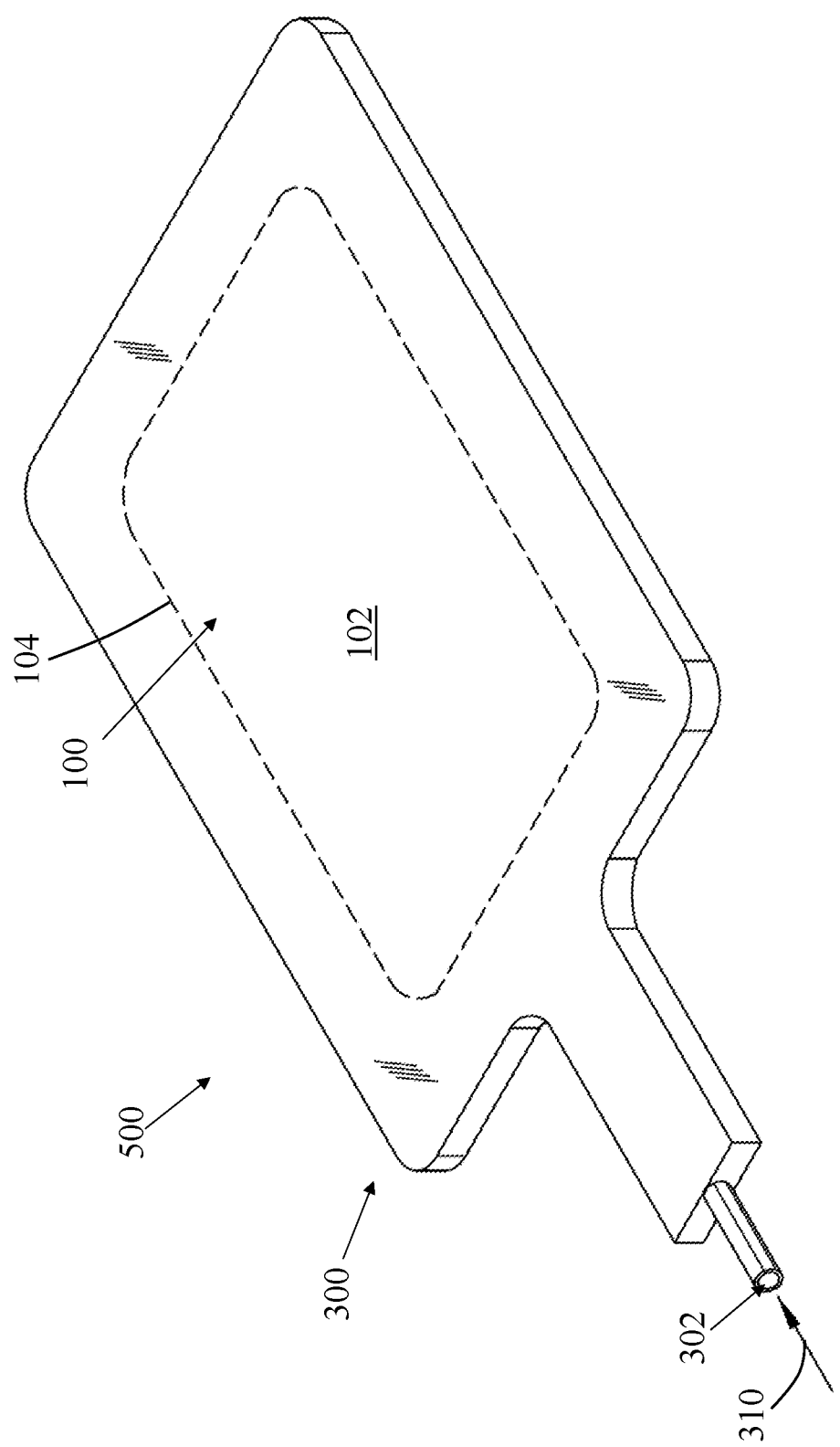
FIG. 5 is an upper perspective view of an exemplary medical gauze and gas flow assembly, in accordance with the present invention.

FIG. 5 shows the assembly 500 from a top view, illustrating the gas flow framing structure 300 integrated with a medical dressing cover 100. In one non-limiting embodiment, the lower surface 810 of the medical dressing cover 100 is directly coupled to the gas flow framing structure 300. This creates a parallel relationship, in which the gas flow framing structure 300 and the gas flow channel 312 is embedded in the medical dressing cover 100 with gas flow 310 provided through the gas inlet 302.

Figure 6:
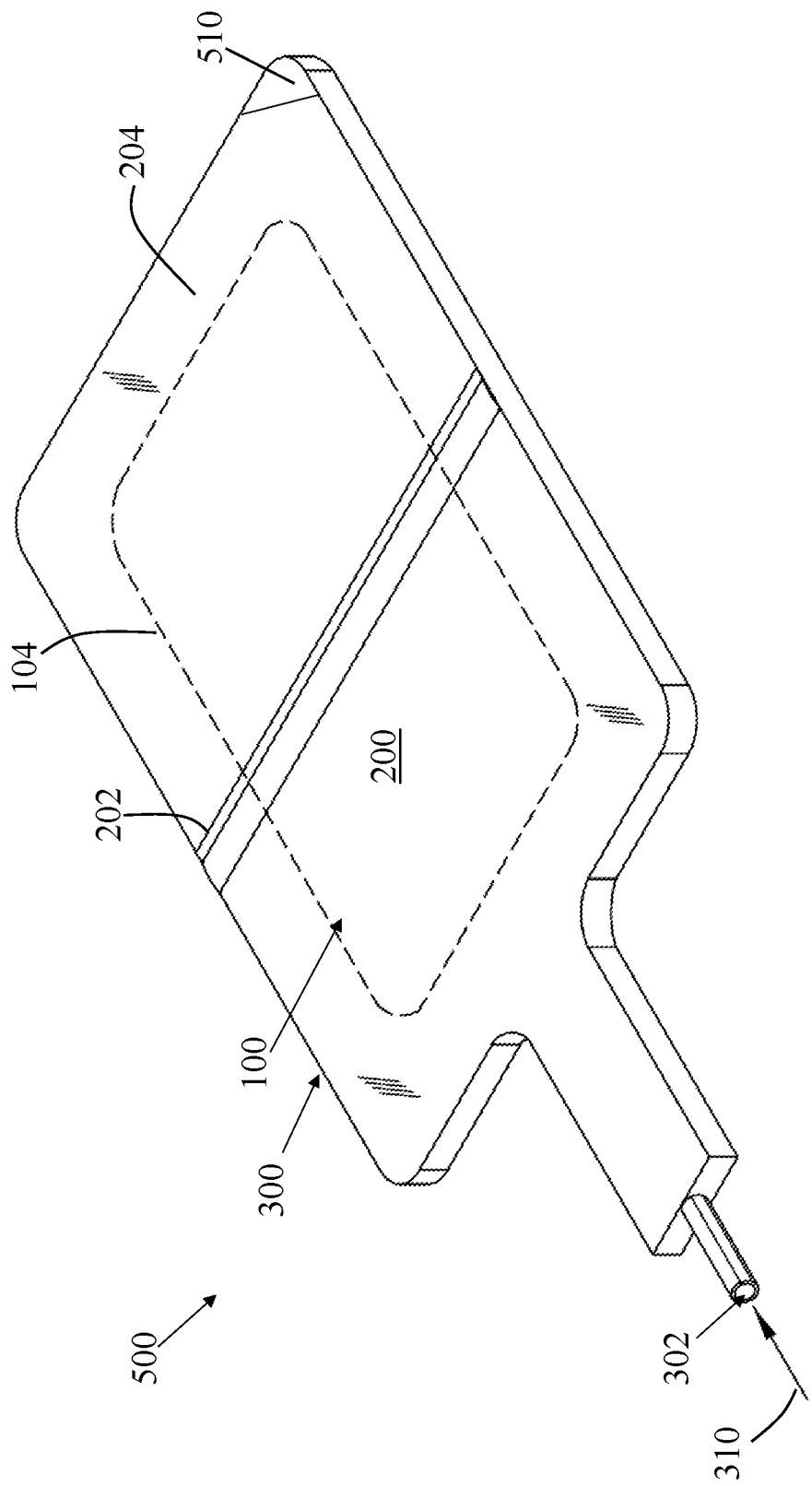
FIG. 6 is a lower perspective view of an exemplary medical gauze and gas flow assembly, in accordance with the present invention.

FIG. 6 shows the assembly 500 from a bottom view illustrating the flexible polymeric release liner 202 covering to the medical dressing cover upper layer 102 lower surface 204. Adhesive is located on the lower surface 204 to provide attachment to the skin around the wound. A detachment tab 510 corner area or protrusion is may be disposed without adhesive. The polymeric release liner 202 is removed prior to use to expose the adhesive on lower surface 204 and expose the lower surface of the lower layer 200. The adhesive has properties common to existing wound care products that enables easy-on, easy-off skin interface (such as silicone-based adhesives).

The gas flow 310 provided at the gas inlet 302 of a nozzle or other part of tubing 318 comprises a gas, such as air, oxygen, or other regenerative gas, set at gas inlet 302 pressure to cause the gas to flow over the wound treatment area 800 to the ambient environment. Those skilled in the art will recognize that such gases work to optimize healing of a wound on the skin. In some embodiments, the gas provided may be sourced from standard respiratory gas sources such as a nebulizer pump, an oxygen concentrator, pressurized oxygen tank, or hospital room wall oxygen as used in the medical field.

As referenced in FIGS. 7a and 7b, the inner surface 306, the outer surface 304, the external perimeter attachment area 440 and the internal perimeter attachment area 445 of the gas flow framing structure 300 define a gas flow channel 312 that is in fluid communication with the gas inlet 302. The gas flow channel 312 is sized and dimensioned to substantially surround the perimeter boundary 104 of the lower layer 200 of the medical dressing cover 100, The lower layer 200 described above is the medical grade gauze material 700. The gas flow channel 312 is also configured to circumambulate a medical grade gauze material 700, described below. The upper surface 810 of the gas flow framing structure 300 is directly coupled to the lower surface of the upper layer 102 of the medical dressing cover 100. The enclosure area of the gas flow channel 312 surrounds the wound treatment area 800, such that the wound is substantially enclosed.

Figure 8:
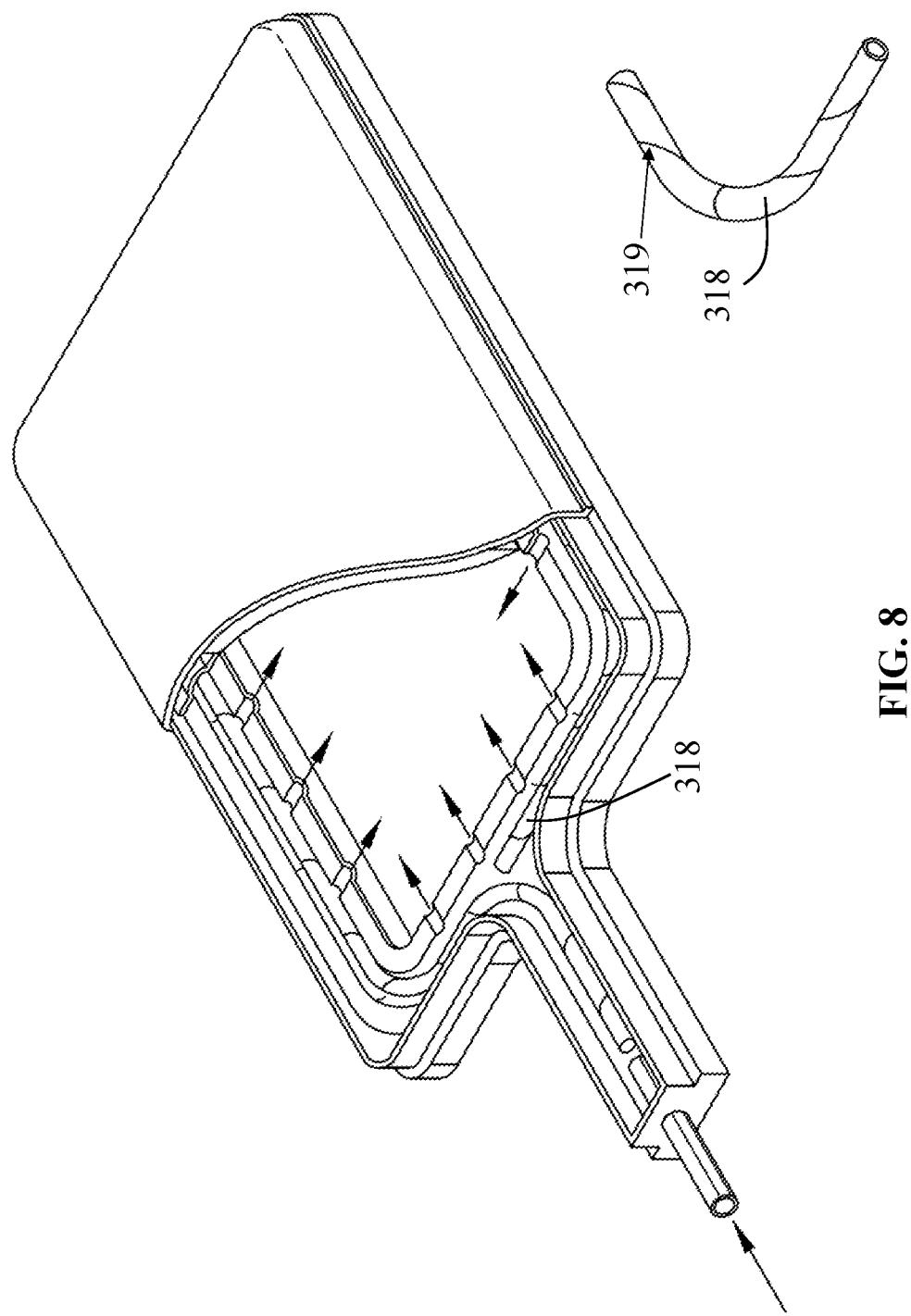
FIG. 8 is an upper perspective view of the medical gauze and gas flow assembly, showing a partial cutaway of the medical dressing cover and the upper layer of the gas flow framing structure with the spiral tubing in the gas flow channel, in accordance with the present invention.

There are wound treatment applications such as bed sores where body pressure can create constrictions of the gas flow channel 312 and prevent gas flow to the gas outlet 308a-n. As shown in FIG. 8, an alternate embodiment of the gas flow framing structure 300 incorporates a spiral tubing 318 that traverses inside the length of the gas flow channel 312 from the termination of the gas inlet 302 for the complete length of the gas flow channel 312. The spiral tubing 318 is a hard polymer that maintains shape when compressed. The spirals in the tubing achieves the required flexibility to traverse around the bends in the gas flow channel 312 and allows for the gas to flow through the spiral gaps 319 and through tubing center to flow around the constricted areas of the gas flow channel 312. This embodiment is utilized when the wound application requires operation during constrictions due to compression of the gas flow channel 312.

Figure 7:
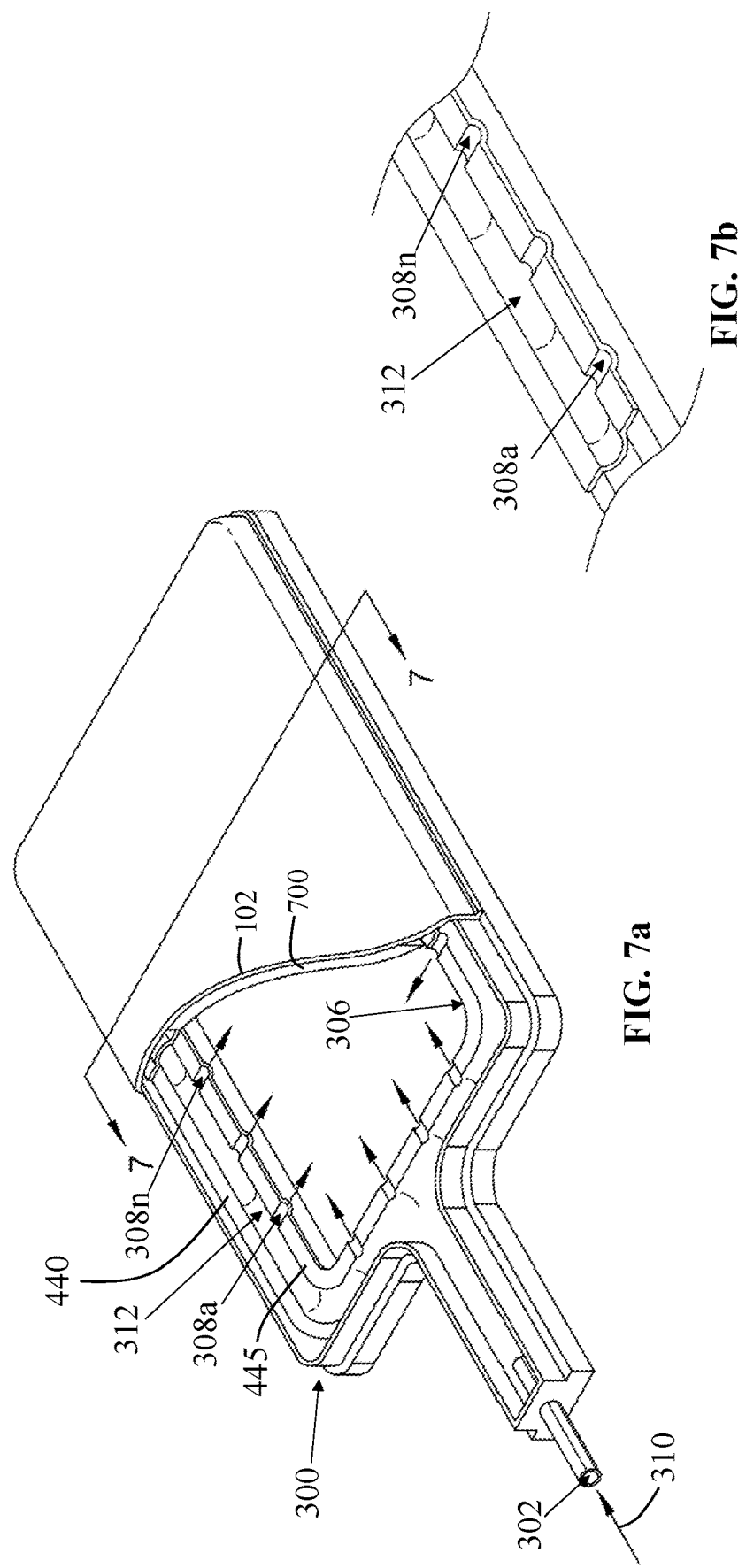
FIGS. 7a and 7b are an upper perspective view of the medical gauze and gas flow assembly, showing a partial cutaway of the medical dressing cover and the upper layer of the gas flow framing structure, in accordance with the present invention.

In one non-limiting embodiment, the gas flow channel 312 forms a rectangular shape. However, in other embodiments, the shape and dimensions of the gas flow channel 312 is adapted to accommodate different parts of the body. For example, FIG. 7 shows the gas flow channel 312 defined by a generally rectangular shape. Despite the shape of the gas flow channel 312, the gas discharges approximately within the enclosed area of the inner surface 306. This requires that the wound treatment area 800 is substantially enclosed within the gas flow channel 312 so that the gas flow passes over the wound treatment area 800.

For discharge of the gas 310, a plurality of enclosed gas outlets 308a-n are disposed on the inner surface 306 of the gas flow framing structure 300, downstream, and in fluid communication with the gas inlet 302 and the gas flow channel 312. The enclosed gas outlets 308a-n serve as the discharge points from the gas flow framing structure 300, and may comprise multiple, equally spaced-apart openings disposed across the inner surface 306 of the gas flow framing structure 300. The equal spacing between enclosed gas outlets 308a-n helps create uniform gas flow distribution across the wound. In one structural embodiment, the plurality of enclosed gas outlets 308a-n are disposed on the inner surface 306 of the gas-flow framing structure 300 in a parallel, spaced-apart relationship.

The enclosed gas outlets 308a-n are configured to orient a provided gas flow over a wound treatment area 800 disposed directly below the medical grade gauze material 700 that forms the lower surface of the lower layer 200 of the medical dressing cover 100. FIG. 7 illustrates the enclosed gas outlets 308a-n arranged in a rectangular shape and discharging the gas inwardly towards the wound treatment area 800.

Figure 13:
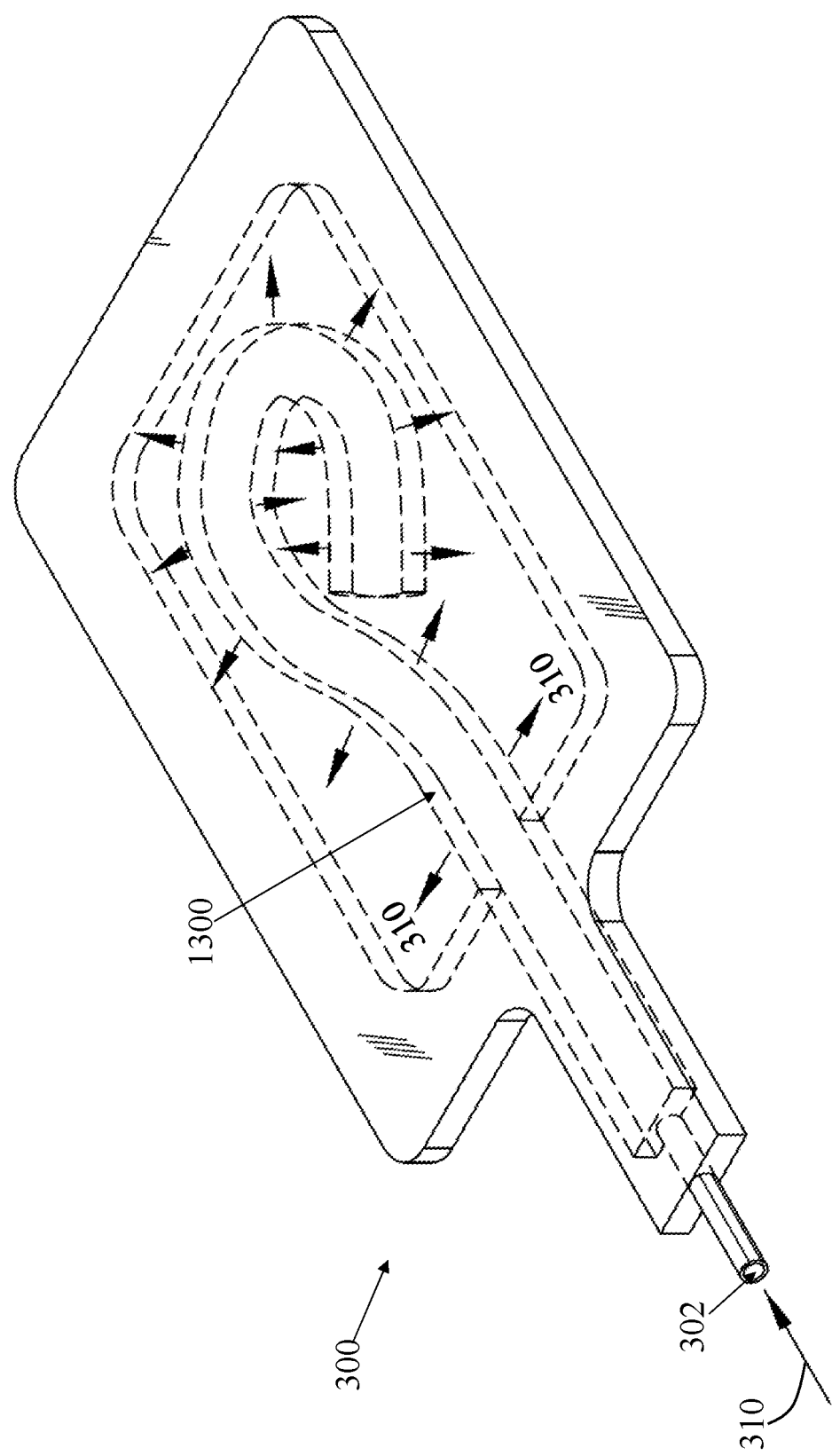
FIG. 13 is an upper perspective view of the gas flow framing structure, showing a hook shaped gas flow channel, in accordance with the present invention.
Figure 14:
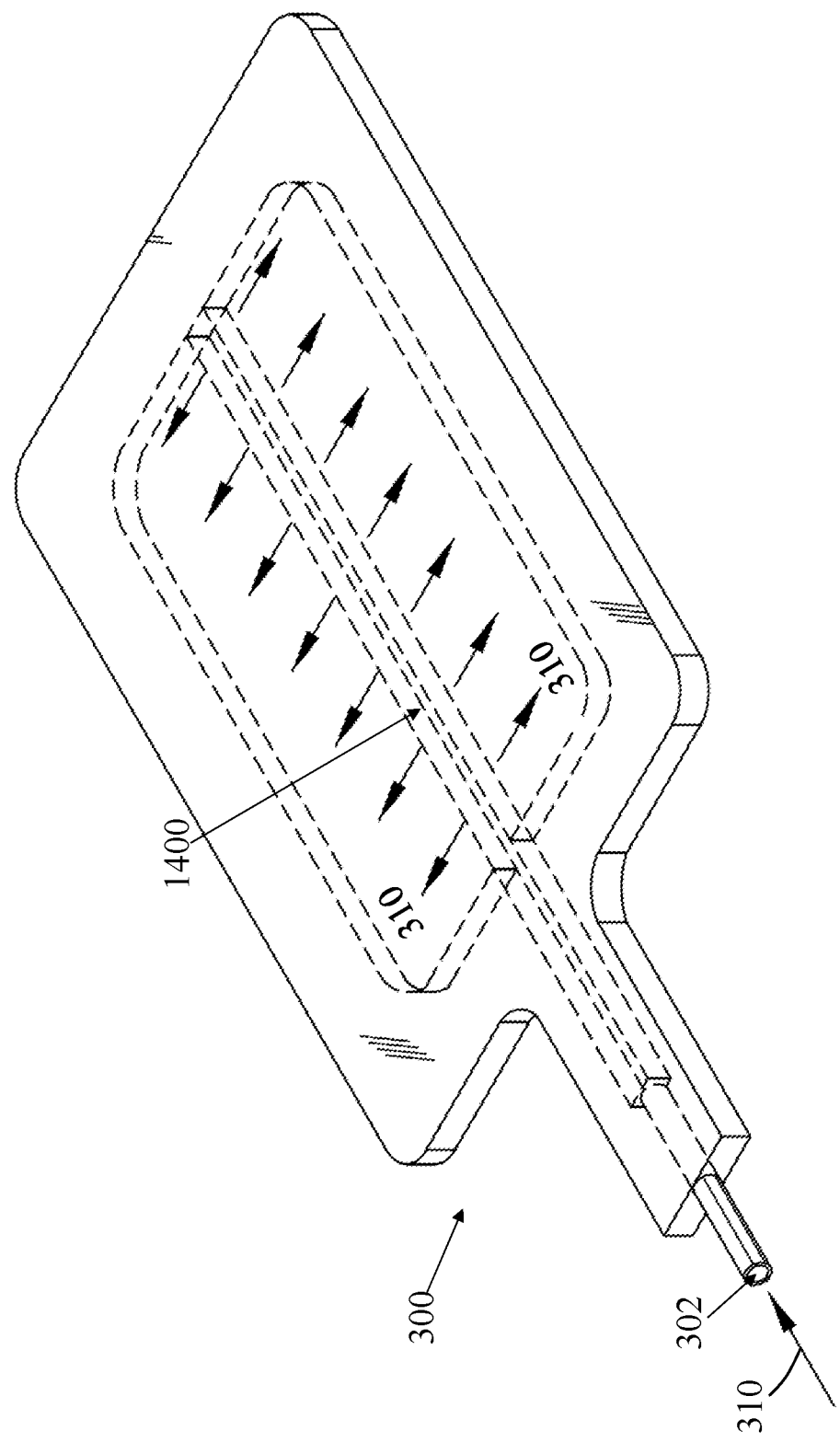
FIG. 14 is an upper perspective view of the gas flow framing structure, showing a linear shaped gas flow channel, in accordance with the present invention.

However, in one alternative embodiment shown in FIG. 13, the enclosed gas outlets 308a-n can be arranged in a hook shape gas flow channel 1300 defined by the shape of the RF weld of the upper 410 and lower 420 layers of the gas flow framing structure 300 that discharges the gas 310 outwardly. This unique hook-shape may be useful for treating irregularly shaped wounds. In yet another alternative embodiment shown in FIG. 14, the enclosed gas outlets 308a-n can be arranged in a linear shape gas flow channel 1400 defined by the shape of the RF weld of the upper 410 and lower 420 layers of the gas flow framing structure 300 that discharges the gas 310 outwardly. This unique linear shape may be useful for treating elongated wounds, such as cuts. In any case, the medical dressing cover 100 and the medical grade gauze material 700 operate in substantially the same manner with any of the shapes for the gas flow channels 1300, 1400.

Figure 9:
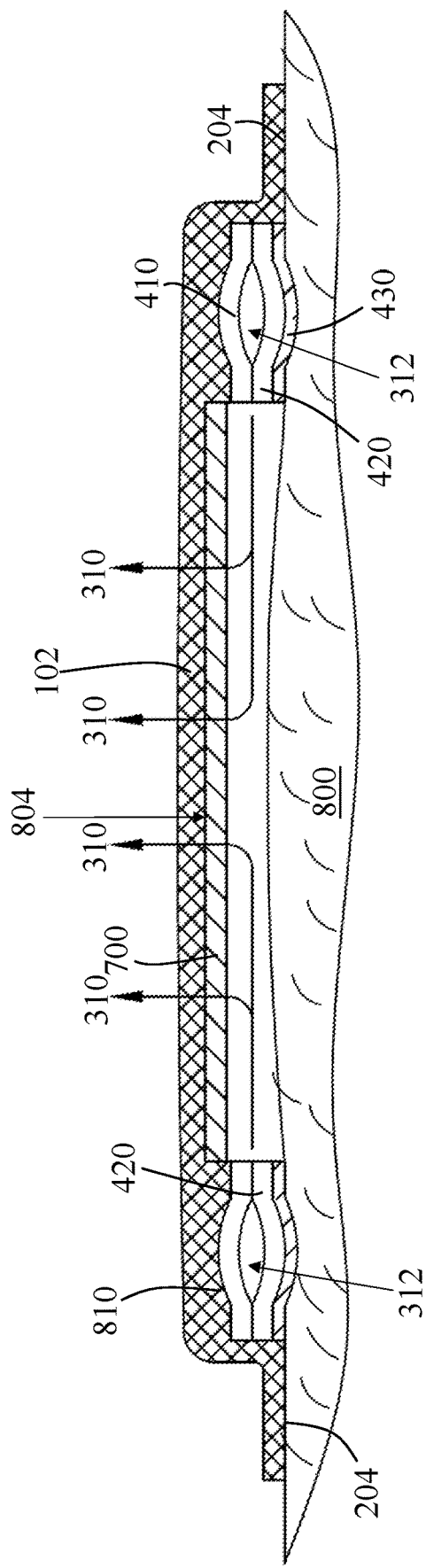
FIG. 9 is a sectioned side view of the medical gauze and gas flow assembly, the section taken along section 7-7 of FIG. 7, in accordance with the present invention.

The medical dressing cover 100 is configured to work in conjunction with the gas flow framing structure 300. As shown in FIG. 9, a cross section view 7-7 from FIG. 7, the medical dressing cover 100 integrates with the gas flow framing structure 300, with each component providing a different, but important function for treating the wound. In this manner, the medical dressing cover 100 encloses the wound treatment area 800, while also orienting the gas flow framing structure 300, such that the enclosed gas outlets 308a-n thereof, orient towards the wound treatment area 800. In this embodiment, the gas flow framing structure 300 is fixedly adhered, coplanar to the medical dressing cover 100 upper layer 102 lower surface 810 to orient the gas flow towards the wound.

In addition, the medical dressing cover 100 also has an upper layer 102 that is defined by a woven gas-permeable material or a polymeric material that is not gas-permeable configured with an array or distribution of vent holes to achieve gas-permeability. Such a material is effective for allowing gas to vent after engaging the wound treatment area 800. The upper layer 102 has a lower surface 804 superimposed over and directly coupled to the medical grade gauze material 700. Additionally, the upper layer 102 has adhesive located on the lower surface 204 outside the perimeter boundary 104 to provide attachment to the skin around the wound. The adhesive has properties common to existing wound care products that enables easy-on, easy-off skin interface (such as silicone-based adhesives).

As seen in the above embodiments the thin layers form a planar structure that covers the wound treatment area. The functions provided by each layer can be arranged in various configurations. The three primary functional layers are the medical dressing cover 100, the medical grade gauze material 700 and the gas flow framing structure 300. These three layers, located above the skin, provide the fundamental operation of the assembly 500 to improve wound healing. In the prior embodiments the upper layer 102 of the medical dressing cover 100 completely encompasses the assembly 500 and provides the attachment to the skin achieving containment of the wound exudate. For all embodiments the attachment around the skin is non-critical and considered to be non-occlusive because the attachment does not affect the gas flow over the wound treatment area. For some wound treatment configurations the attachment to skin can be discontinuous allowing gas flow to ambient along the skin. As shown in the various embodiments, additional features such as a comfort layer and soft foam stand-offs around the perimeter of the wound treatment area may provide improved wound healing.

Figure 10:
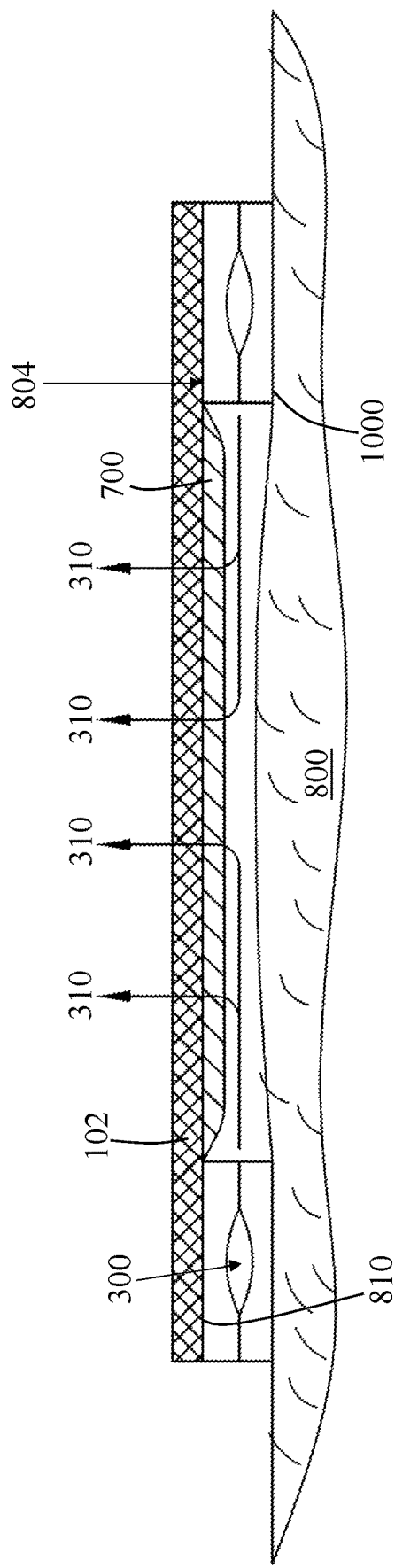
FIG. 10 is a sectioned side view of a 2-layer embodiment of the medical gauze and gas flow framing structure, in accordance with the present invention.

A 2-layer embodiment shown in FIG. 10 illustrates direct coupling of the gas flow support frame 300 around the perimeter of the lower surface 810 of the upper layer 102 of the medical dressing cover 100. The medical dressing cover upper layer 102 and the medical dressing material 700 combined to form one layer. In this embodiment the gas flow framing structure 300 lower surface 1000 is adhered directly to the skin. The adhesive has properties common to existing wound care products that enables easy-on, easy-off skin interface (such as silicone-based adhesives). A corner area or protrusion detachment tab 510 may be provided that does not have adhesive to facilitate removal from the skin.

Figure 11:
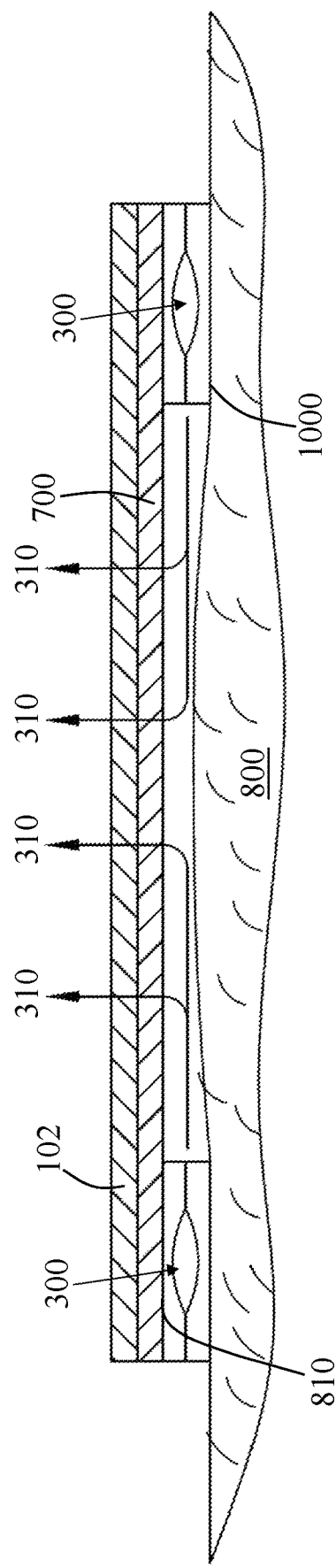
FIG. 11 is a section side view of a 3-layer embodiment of the medical gauze and gas flow framing structure, in accordance with the present invention.

A 3-layer embodiment shown in FIG. 11 illustrates the medical gauze material 700 is fixedly attached between the lower surface of the upper layer 102 of the medical dressing cover 100 and the upper surface 810 of the gas flow framing structure 300. In this embodiment the gas flow framing structure 300 lower surface 1000 is adhered directly to the skin. The adhesive has properties common to existing wound care products that enables easy-on, easy-off skin interface (such as silicone-based adhesives). A corner area or protrusion detachment tab 510 may be provided that does not have adhesive to facilitate removal from the skin.

Figure 12:
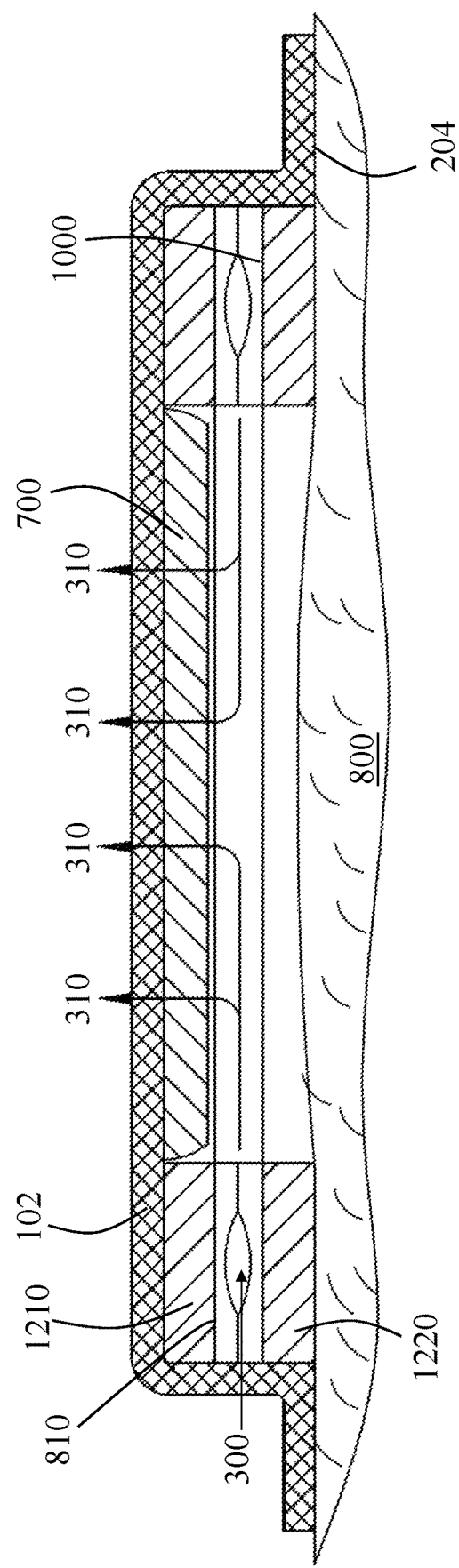
FIG. 12 is a section side view of an embodiment with foam stand-offs of the medical gauze and gas flow framing structure, in accordance with the present invention.

Another embodiment shown in FIG. 12 illustrates where soft foam stand-offs may be located. An upper foam stand-off 1210 is located on the upper surface 810 of the gas flow framing structure and a lower foam stand-off 1220 is located on the lower surface 1000 of the gas flow framing structure. The foam stand-offs 1210, 1220, applied to the prior embodiments provide a larger gas volume over the wound treatment area 800 and facilitate thicker medical grade gauze material 700. The medical dressing cover upper layer 102 completely encompasses the assembly 500 providing the adhesive attachment to the skin 204. All of these previously discussed embodiments are removed and replaced as a complete assembly 500.

Figure 17:
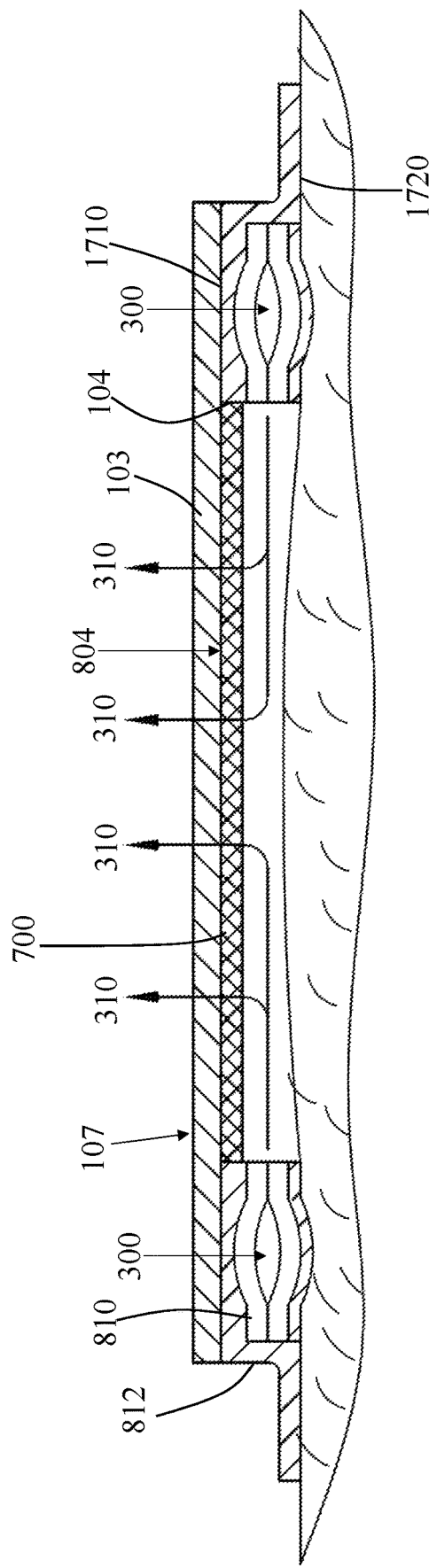
FIG. 17 is a sectioned side view of the medical gauze and gas flow assembly with a replaceable medical dressing cover, the section taken along 17-17 in FIG. 15, in accordance with the present invention.

As an alternate embodiment as shown in FIG. 15, the medical dressing cover upper layer 102 is reconfigured to allow removal and replacement of a replaceable medical dressing cover 107 while the gas flow framing structure 300 remains attached to the skin and the gas flow connections are maintained during gauze replacement. As shown in FIG. 16 cross section 15-15 of FIG. 15, the upper layer 103 has a lower surface 1610 that is configured to provide a removable adhesive interface of the medical dressing cover 100 to the upper surface 1710 of gas flow support frame 812. The 17-17 cross sectional shown in FIG. 17 illustrates the direct coupling of the lower surface 804 of the upper layer 102 of the replaceable medical dressing cover 107 attached to the medical dressing gauze material 700 within the external perimeter 104 of the medical grade gauze material and located over the wound treatment area. The gas flow support frame 812 lower surface inner perimeter is directly coupled to upper surface 810 of the gas flow framing structure 300. The lower surface 804 of the replaceable medical dressing cover 107 overlaps the inner perimeter of the upper surface 1710 of gas flow support frame 812. An adhesive material on the lower surface 804 removably attaches to the upper surface 1710 of the gas flow support frame 812. A separate adhesive attachment around the outer perimeter of the lower surface 1720 removably attaches to the skin.

For this embodiment, the removal of the replaceable medical dressing assembly 107 is achieved with a detachment tab 105 without adhesive such that pulling applies forces to separate the removable adhered surfaces 1710 of the replaceable medical dressing cover 107 from the gas flow support frame 812.

It is significant to note that the removable adhesive bonding material at interface 1710 is of a bonding strength property equal-to or less than the bonding strength of the adhesive bonding material disposed on the lower surface 1720 of the gas flow support frame 812. In this manner, the gas flow support structure 812 remains firmly adhered to the skin, while the removable medical dressing cover 107 and the medical grade gauze material 700 are easily removed and replaced with fresh coverings and gauze materials.

Figure 19:
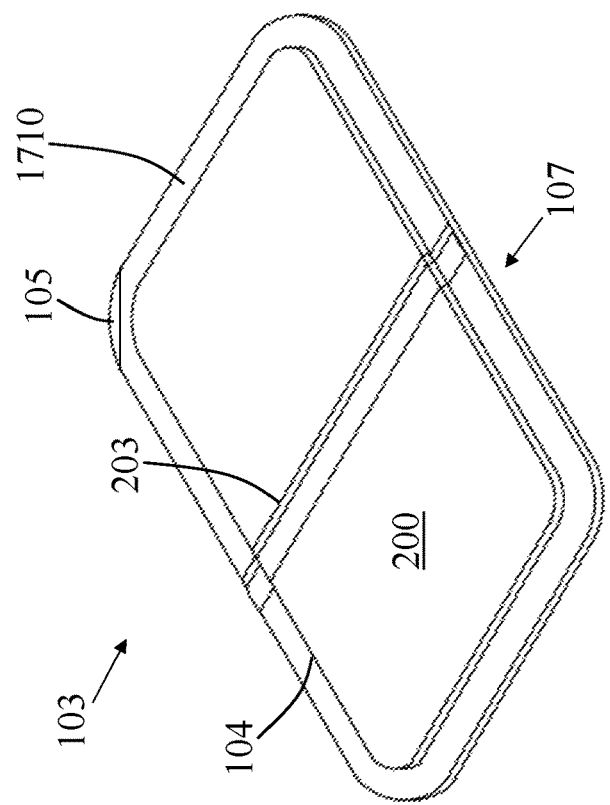
FIG. 19 is a bottom view of the replaceable medical dressing cover, in accordance with the present invention.
Figure 18:
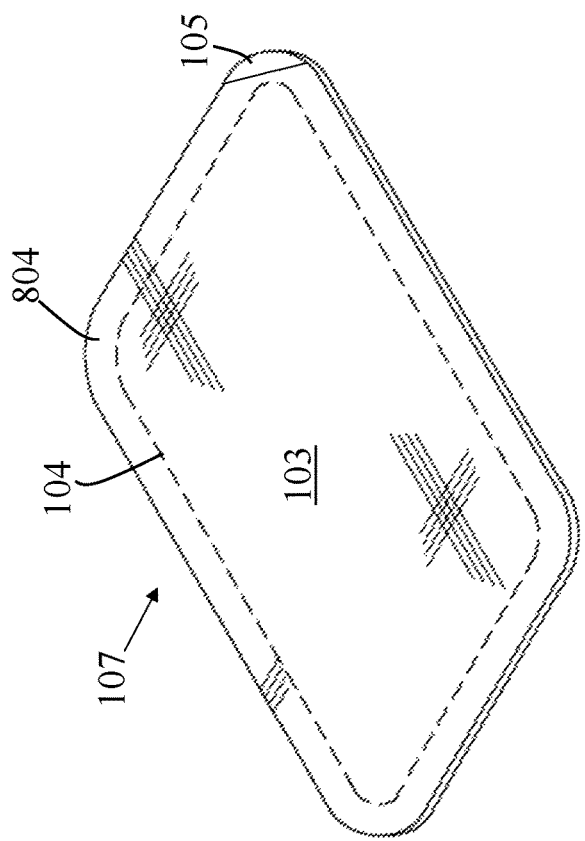
FIG. 18 is a top view of the replaceable medical dressing cover, in accordance with the present invention.
Figure 20:
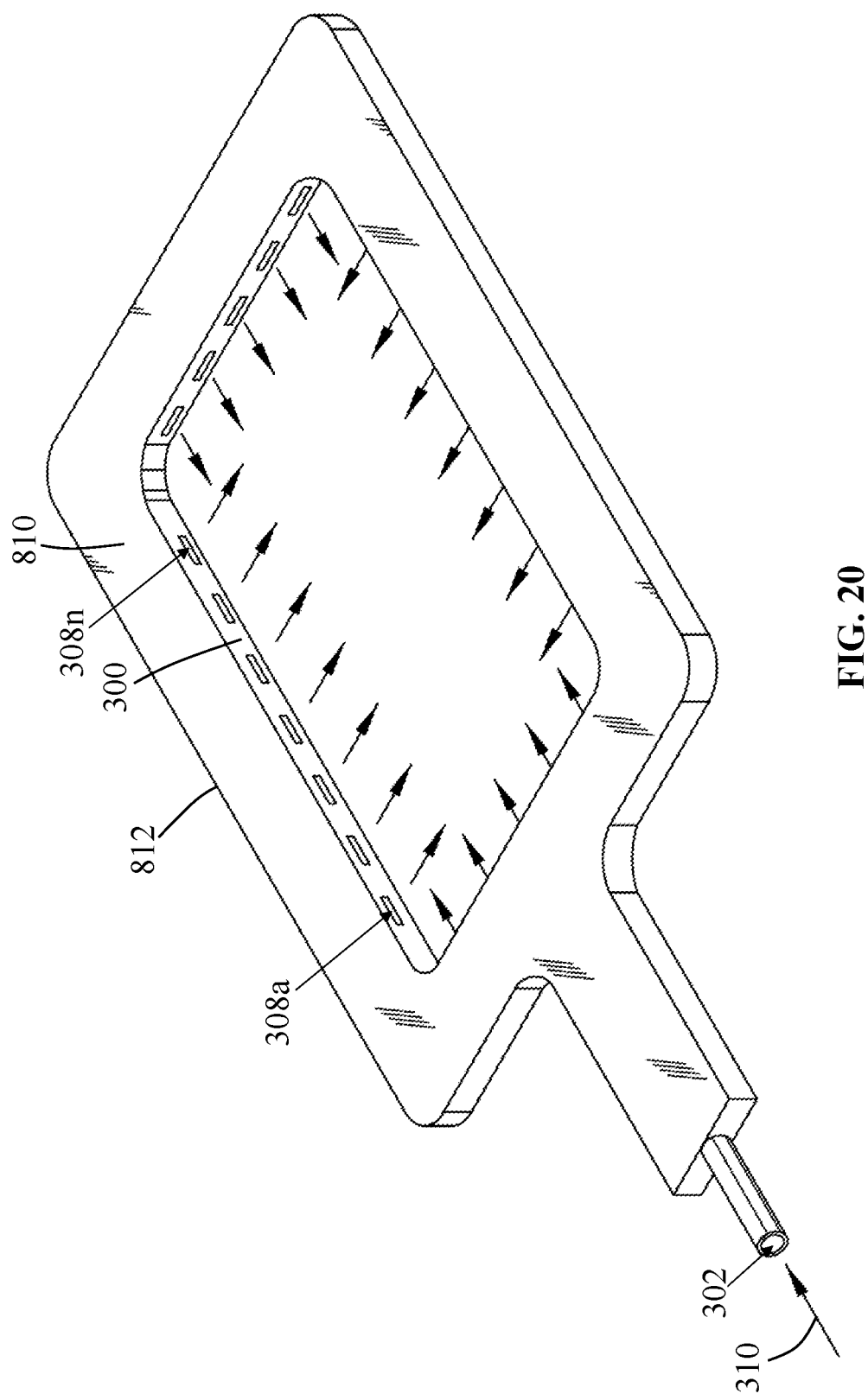
FIG. 20 is an upper perspective of the gas flow framing structure and the gas flow support frame, showing the gas outlets with the replaceable medical dressing cover removed, in accordance with the present invention.

The top view of the replaceable medical dressing cover 107 is shown in FIG. 18 with an upper layer 103 that is defined by a gas-permeable material. The bottom view of the replaceable medical dressing cover 107 is shown in FIG. 19 illustrating the flexible polymeric release liner 203 that completely covers surfaces 200 and 1710 prior to usage. When the release line is removed the adhesive surface around the perimeter surface 1710 is exposed to allow attachment of the removable medical dressing cover 107 to the gas flow support frame 812 upper surface 1710. Also, the medical grade gauze material 700 lower surface 200 covers the wound treatment area 800 when the replacement medical dressing cover 107 is in place. FIG. 20 illustrates the gas frame support structure 812 attached to the gas flow support frame 300 when the removable medical dressing cover 107 is removed. In this configuration the wound treatment area 800 is expose for visual inspection and treatment. The implementation of the removable medical dressing cover 107 is illustrated in one embodiment of the layering but is applicable to all the variations of the layering configurations shown in prior embodiments herein.

In some embodiments, the medical grade gauze material 700 serves to absorb fluids from the wound treatment area 800, while gas passes over the wound treatment area 800. In one non-limiting embodiment, the medical grade gauze material 700 is a weave of cotton and synthetic fibers that are air permeable, and absorbent. The medical grade gauze material 700 is also easily replaceable, as discussed above by either replacing the complete assembly 500 or the replaceable medical dressing cover 107.

In operation, the assembly 500 is applied directly over the wound treatment area 800, with the enclosed gas outlets 308a-n directing the gas inwardly to the wound treatment area 800. The gas flow 310 vents to ambient through the gas-permeable, medical grade gauze material 700 and through the gas-permeable upper layer 102 103 of the medical dressing cover 100 107 after flowing over the wound.

The synergistic combination of a medical grade gauze material 700 that is gas permeable and does not stick to wounds, with a gas flow framing structure 300 that carries the gas flow 310 over the wound treatment area 800 works to enhance the efficacy for healing a wound. And, when the medical grade gauze material 700 is degraded/soiled, the complete assembly 500 can be removed and replaced using a detachment tab 510 or the replaceable medical dressing cover 107 is detached using detachment tab 105 to separate lower surface 804 of the medical dressing cover 107 from the gas flow support frame 812 upper surface 1710, and applying a fresh replaceable medical grade cover 107 including fresh medical gauze material 700 thereto.

Figure 21:
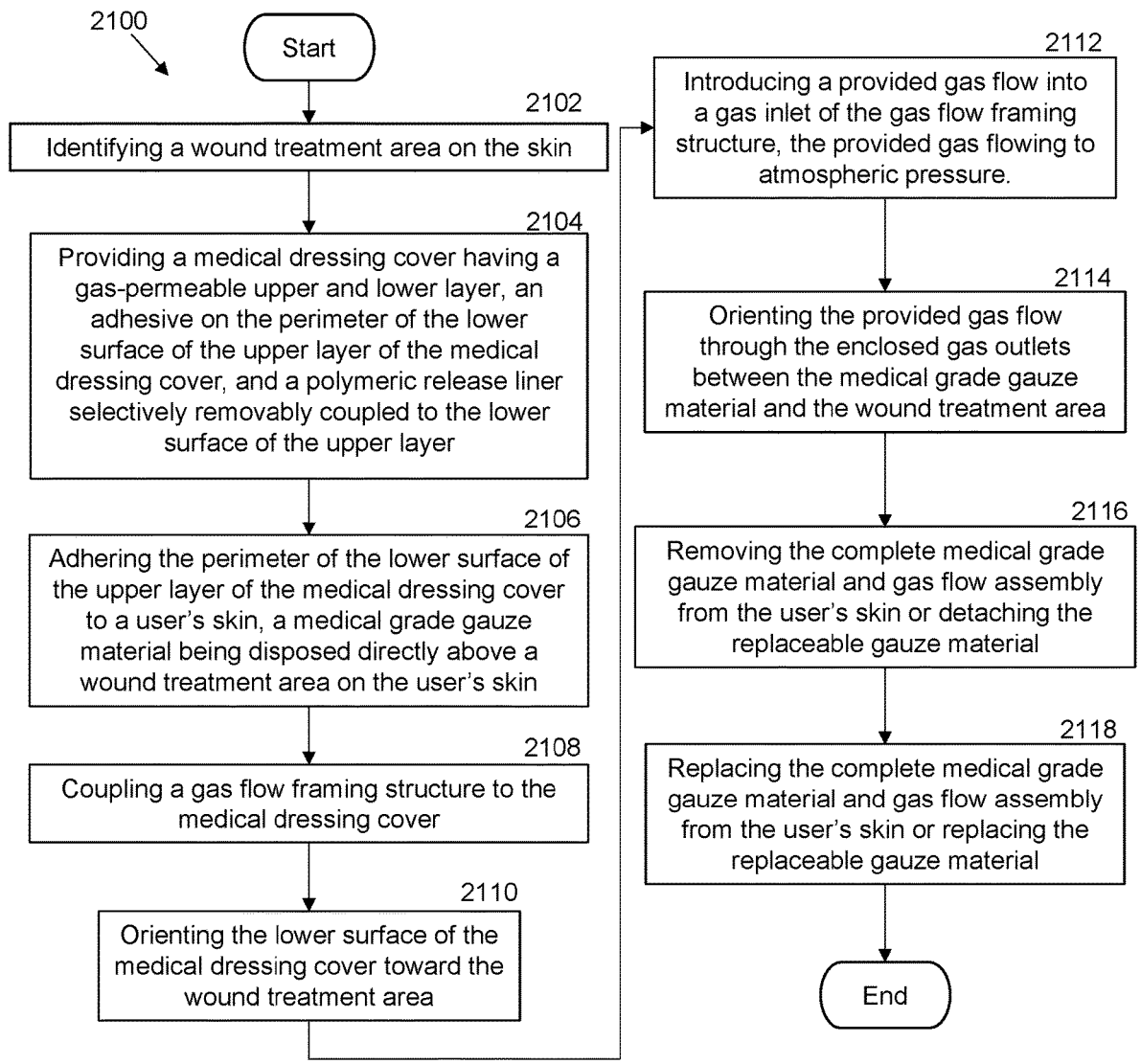
FIG. 21 is a flowchart of an exemplary method of applying a medical gauze with directed gas flow on a wound, in accordance with the present invention.

FIG. 21 will be described in conjunction with the process flow chart. Although FIG. 21 shows a specific order of executing the process steps, the order of executing the steps may be changed relative to the order shown in certain embodiments. Also, two or more blocks shown in succession may be executed concurrently or with partial concurrence in some embodiments. Certain steps may also be omitted in FIG. 21 for the sake of brevity. In some embodiments, some or all of the process steps included in FIG. 21 can be combined into a single process.

A method 2100 of applying a medical gauze with gas flow assembly over a wound treatment area serves to enhance healing of the wound, by simultaneously applying a gas permeable medical grade gauze material to the wound for absorbing fluids and protecting against infections and flowing gas over the wound treatment area for drying effects provided. The method 2100 may include an initial Step 2102 of identifying a wound treatment area on the skin. The wound may include a laceration, burn, pressure ulcers, bed sores, decubitus ulcers or other superficial wound known in the medical art. These types of wound exhibit different conditions for treatment such as certain wounds dressings will see conditions where under certain circumstances there may be external pressure applied to the wound dressing due to body positioning compression of the wound dressing.

The method 2100 may further comprise a Step 2104 of providing a medical dressing cover having a flexible, gas-permeable upper and lower layer. An adhesive disposed around the perimeter of lower layer on the lower surface of the upper layer of the medical dressing cover, and a flexible polymeric release liner selectively removably coupled to perimeter of the lower surface of the upper layer of the medical dressing cover. The medical dressing cover is configured to overlay the wound.

A Step 2106 includes adhering a medical grade gauze material lower layer to the upper layer lower surface of medical dressing cover, the medical grade gauze material being disposed directly above a wound treatment area, whereby the medical grade gauze material enhances the treatment of the wound treatment area. The medical grade gauze material can be removed and replaced with a complete new medical gauze and gas flow assembly or, for another embodiment, removal and replacement of only the replaceable medical dressing cover that includes fresh medical grade gauze material. The medical grade gauze material being disposed directly above the wound treatment area.

Step 2108 comprises coupling a gas flow framing structure to the medical dressing cover, the gas flow framing structure defining a gas inlet, a gas flow channel within the upper and lower layers of gas flow framing structure, and a plurality of enclosed gas outlets operably configured and oriented to direct a provided gas flow therethrough. The gas flow enhances the treatment of the wound. Evaluation is performed to determine whether the treatment condition of the wound result in bodily compression of the wound dressing. If bodily compression of the wound dressing conditions will exist during treatment then select the gas flow framing structure with a spiral tubing traversing the gas flow channel. If bodily compression of the wound dressing will not occur (such as external locations on leg or arm skin) then the spiral tubing in not required.

Step 2110 includes orienting the lower surface of the medical dressing cover towards the wound treatment area and adhering to the skin around the wound after the polymeric release liner is removed. This allows for the lower layer of the medical dressing cover to absorb bodily fluids and cover the entirety of the wound.

A Step 2112 includes introducing the provided gas flow into the gas inlet of the gas flow framing structure, the gas is provided at sufficient pressure to inflate the gas flow channel. The provided gas flow may be sourced from standard respiratory gas sources such as a nebulizer pump, an oxygen concentrator or pressurized oxygen tank or hospital room wall oxygen, as used in the medical field that are capable of gage pressure in the range from 0.1 psi to 2.5 psi.

A Step 2114 comprises directing the provided gas flow through the plurality of enclosed gas outlets and to the wound treatment area disposed between the medical grade gauze material forming the lower surface of the medical dressing cover and the wound treatment area. The gas vents to ambient out of the gas-permeable and flexible upper and lower layers of the medical dressing cover. When the dressing is saturated or degraded the method 2100 may further comprise a Step 2116 of removing the complete medical gauze and gas flow assembly by separating the lower surface of the medical dressing cover from the skin using the detachment tab. In another embodiment, the medical gauze material can be removed by pulling the detachment tab separating the removable medical grade cover from the upper surface of the gas flow support frame. A final Step 2118 includes replacing the complete medical gauze and gas flow assembly or replacing the replaceable medical dressing cover to provide a fresh medical grade gauze material over the wound.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the above described features.

What is claimed is:

1. A medical gauze and gas flow assembly comprising:
   a medical dressing cover with a lower surface, having a gas-permeable and flexible upper layer with a lower surface forming at least a portion of the lower surfaces of the medical dressing cover, a flexible lower layer directly coupled to the upper layer, an adhesive disposed on the lower surface of the upper layer and around a perimeter of the lower layer, a flexible polymeric release liner selectively removably coupled to the lower surface of the medical dressing cover;
   a medical grade gauze material forming at least a portion of the lower layer of the medical dressing cover and flanked on its two opposing sides by the flexible upper layer; and
   a gas flow framing structure coupled to the medical dressing cover, with an outer surface and an inner surface opposing the outer surface of the gas flow framing structure, and defining a gas inlet, a gas flow channel within the upper and lower layers of gas flow framing structure, and a plurality of enclosed gas outlets disposed on the inner surface of the gas flow framing structure and downstream of the gas inlet, the plurality of enclosed gas outlets each operably configured to orient the provided gas flow between the medical grade gauze material forming the lower surface of the medical dressing cover and the wound treatment area.

2. The assembly according to claim 1, wherein the gas flow framing structure further comprises:
   a plurality of elastic valves defining the plurality of enclosed gas outlets disposed on the inner surface of the gas flow framing structure.

3. The assembly according to claim 2, wherein:
   the plurality of elastic valves each include a slot between the upper and lower layers on the inner perimeter area of the gas flow framing structure operable to allow passage of the provided gas flow when a predetermined amount of gas pressure is applied to the gas inlet.

4. The assembly according to claim 1, wherein the medical dressing cover further comprises:
   a lower surface perimeter with the adhesive disposed thereon for attachment to the skin.

5. The assembly according to claim 4, wherein:
   the lower surface around the perimeter contains a detachment tab on a corner area or protrusion that does not have adhesive.

6. The assembly according to claim 4, wherein:
   the lower surface perimeter surrounds the medical grade gauze material.

7. The assembly according to claim 4, wherein:
   the gas flow channel within the gas flow framing structure substantially surrounds the medical grade gauze material that includes a flexible spiral tubing that transverses the length of the gas flow channel.

8. The assembly according to claim 1, wherein:
   the plurality of enclosed gas outlets are operably configured to orient the provided gas flow between to the medical grade gauze material forming the lower surface of the medical dressing cover and the wound treatment area, and the gas flows through the gas-permeable and flexible upper and lower layers of the medical dressing cover.

9. The assembly according to claim 8, wherein:
the plurality of enclosed gas outlets are disposed on the inner surface of the gas flow framing structure in a parallel, spaced-apart relationship.

10. The assembly according to claim 1, wherein:
the gas flow channel within the gas flow framing structure contains a hard-plastic spiral tubing that transverses the length of the gas flow channel.

11. The assembly according to claim 1, wherein:
the gas flow framing structure is directly coupled to the lower surface of the upper layer of the medical dressing cover.

12. The claim according to claim 1:
the gas flow framing structure lower surface is directly coupled to a comfort layer around the perimeter of the wound treatment area made of soft cotton or equivalent.

13. The claim according to claim 12, wherein:
the gas flow framing structure is coupled to a upper foam stand-off layer located between the medical dressing cover and the gas flow framing structure upper surface and to a lower foam stand-off layer located between the lower surface of the gas flow framing structure and the skin, around the perimeter of the wound treatment area.

14. The assembly according to claim 1, wherein:
the medical grade gauze material is disposed directly above the wound treatment area.

15. The assembly according to claim 14, wherein:
the medical grade gauze material and the upper layer of the medical dressing cover are operably configured to vent the gas flowing over the wound treatment area to an ambient environment.

16. The assembly according to claim 15, wherein:
the medical grade gauze material is operably configured to absorb fluids from the wound treatment area.

17. A method of applying a medical gauze with directed gas flow on a wound, comprising:
identifying a wound treatment area on the skin;
providing a medical dressing cover with a lower surface, having a gas-permeable upper layer with a lower surface forming at least a portion of the lower surfaces of the medical dressing cover and a lower layer directly coupled to the upper layer, an adhesive disposed on the lower surface of the upper layer and around a perimeter of the lower layer, a polymeric release liner selectively removably coupled to lower surface of the upper layer, and a medical grade gauze material forming at least a portion of the lower layer of the medical dressing cover;
removing the polymeric release liner to expose the adhesive disposed on the lower surface of the upper layer and adhering a medical grade gauze material upper surface to the lower surface of the upper layer of the medical dressing cover, the medical grade gauze material being disposed directly above the wound treatment area;
coupling a gas flow framing structure to the medical dressing cover, the gas flow framing structure defining a gas inlet, a gas flow channel within the upper and lower layers of the gas flow framing structure, and a plurality of enclosed gas outlets operably configured to orient the provided gas flow therethrough, use spiral tubing in the gas flow channel wound dressing with bodily compression;
orienting the lower surface of the medical dressing cover towards the wound treatment area;
introducing the provided gas flow into the gas inlet of the gas flow framing structure, the provided gas pressure inflates the gas flow channel and flows to atmospheric pressure;
orienting the provided gas flow through the enclosed gas outlets between the medical grade gauze material forming the lower surface of the medical dressing cover and the wound treatment area, and the gas flows through the gas-permeable and flexible upper and lower layers of the medical dressing cover;
either removing the complete medical gauze and gas flow assembly from the skin or detaching the replaceable medical dressing cover from the gas flow support frame; and
either replacing the complete medical gauze and gas flow assembly or the replaceable medical dressing cover for a fresh medical grade gauze material.

* * * * *